(12) United States Patent
Drevik et al.

(10) Patent No.: US 7,156,832 B2
(45) Date of Patent: Jan. 2, 2007

(54) ABSORBENT ARTICLE HAVING A STIFFENING ELEMENT AND ELONGATE THROUGH-HOLE

(75) Inventors: Solgun Drevik, Mölnlycke (SE); Fredrik Asp, Onsala (SE); Urban Widlund, Pixbo (SE); Elisabeth Boissier, Vallda (SE)

(73) Assignee: SCA Hygiene Products AB, Gothenburg (SE)

( * ) Notice: Subject to any disclaimer, the term of this patent is extended or adjusted under 35 U.S.C. 154(b) by 374 days.

(21) Appl. No.: 10/310,906

(22) Filed: Dec. 6, 2002

(65) Prior Publication Data

US 2003/0125699 A1 Jul. 3, 2003

Related U.S. Application Data

(60) Provisional application No. 60/336,132, filed on Dec. 6, 2001.

(51) Int. Cl.
*A61F 13/536* (2006.01)
*A61F 13/512* (2006.01)
*A61F 13/47* (2006.01)

(52) U.S. Cl. .............. 604/385.31; 604/383; 604/379; 604/385.01

(58) Field of Classification Search ........ 604/385.31, 604/385.17, 385.01, 385.12, 385.19, 358, 604/385.23, 383, 385.09, 379; D24/124–125
See application file for complete search history.

(56) References Cited

U.S. PATENT DOCUMENTS

| | | | |
|---|---|---|---|
| 3,294,091 A | 12/1966 | Morse | |
| 4,285,343 A | 8/1981 | McNair | |
| 4,608,047 A | 8/1986 | Mattingly | |
| 4,655,759 A | 4/1987 | Romans-Hess et al. | |
| 4,804,380 A | 2/1989 | Lassen et al. | |
| 4,886,513 A * | 12/1989 | Mason et al. | 604/385.31 |
| 5,730,737 A * | 3/1998 | Widlund et al. | 604/378 |
| 5,820,619 A * | 10/1998 | Chen | 604/385.31 |
| 6,210,385 B1* | 4/2001 | Mizutani | 604/385.01 |
| 6,350,257 B1 | 2/2002 | Björklund et al. | |
| 6,470,069 B1* | 10/2002 | Muller | 378/21 |
| 6,554,813 B1* | 4/2003 | Kolby-Falk | 604/385.17 |
| 2002/0065497 A1* | 5/2002 | Kolby-Falk | 604/368 |
| 2003/0125701 A1* | 7/2003 | Widlund | 604/385.31 |

FOREIGN PATENT DOCUMENTS

| | | |
|---|---|---|
| EP | 0 067 465 | 12/1982 |
| EP | 0 130 848 | 1/1985 |
| EP | 0 134 086 | 3/1985 |

(Continued)

*Primary Examiner*—Tatyana Zalukaeva
*Assistant Examiner*—L C Hill
(74) *Attorney, Agent, or Firm*—Buchanan Ingersoll & Rooney PC

(57) ABSTRACT

Absorbent article, such as a sanitary towel, with a stiffening element which is intended to contribute to the three-dimensional shape of the article during its use. The stiffening element is in a plane state before use of the article. The stiffening element has in the rear portion an elongate through-hole which extends in the longitudinal direction of the article and along the centre line of the article, as a result of which the article is during use provided, by virtue of lateral forces arising in the rear portion of the article, with a fold along the longitudinal direction of the article along the hole. The fold extends into the cleft between the buttocks of the wearer during use of the article and in this way stabilizes the article in position on the wearer.

25 Claims, 10 Drawing Sheets

FOREIGN PATENT DOCUMENTS

| | | |
|---|---|---|
| EP | 0 155 515 | 9/1985 |
| EP | 0 298 348 | 1/1989 |
| EP | 0335252 A2 * | 3/1989 |
| EP | 0 335 252 | 10/1989 |
| EP | 0 335 253 | 10/1989 |
| EP | 0 336 578 | 10/1989 |
| EP | 0335252 A2 * | 10/1989 |
| EP | 0 852 938 | 7/1998 |
| EP | 0 956 844 | 11/1999 |
| EP | 0 965 318 | 12/1999 |
| FR | 2 653 328 | 4/1991 |
| SE | 455 668 | 8/1988 |
| SE | 507 798 | 7/1998 |
| WO | WO 97/09014 | 3/1997 |
| WO | WO 9822057 A1 * | 5/1998 |
| WO | WO 9822058 A1 * | 5/1998 |
| WO | WO 99/25282 | 5/1999 |
| WO | WO 9925282 A1 * | 5/1999 |

* cited by examiner

ABSORBENT ARTICLE HAVING A STIFFENING ELEMENT AND ELONGATE THROUGH-HOLE

This application claims priority under 35 U.S.C. § 119 to U.S. Provisional Application No. 60/336,132 entitled ABSORBENT ARTICLE WITH IMPROVED FIT and filed on Dec. 6, 2001, the entire content of which is hereby incorporated by reference.

TECHNICAL FIELD

The present invention relates to an absorbent article, such as a sanitary towel, a panty liner, an incontinent pad, a nappy or the like, which article has a longitudinal direction and a transverse direction, a front portion, a rear portion, a crotch portion located between the rear portion and the front portion, an absorbent element and a liquid-tight layer, and also a stiffening element which is intended to contribute to the three-dimensional shape of the article during its use.

BACKGROUND OF THE INVENTION

A great many different demands are made of absorbent articles, such as a sanitary towel, an incontinence pad, a nappy or the like, which are not easy to satisfy simultaneously. A fundamental requirement is that the article, for example a sanitary towel, should be capable of catching and absorbing bodily fluid discharged from the wearer. Conventional sanitary towels in sizes intended for heavy flows of menstrual fluid have been of thick and relatively wide design. Sanitary towels of this type are described in, for example, U.S. Pat. No. 3,294,091. Thick and relatively wide sanitary towels of this type theoretically have great absorption capacity but in practice, when the sanitary towel is subjected to compression forces when squeezed together between the thighs of the wearer, much of the take-up capacity and absorption capacity is lost. The sanitary towel is squeezed together into an arbitrary rope-like shape which frequently does not offer a sufficiently large receiving surface for the menstrual fluid discharged, and leakage occurs in the case of heavy flows of menstrual fluid. The sanitary towel can also be pressed together between the thighs of the wearer in such a manner that the side edges of the sanitary towel and the liquid-tight layer are folded in over the liquid-permeable surface and in this way reduce the size of the liquid-receiving surface available.

Sanitary towels are intended to be positioned inside a pair of briefs, the design of which may vary. In this connection, sanitary towels can be positioned incorrectly inside the briefs. There is therefore a risk of the sanitary towel being, by mistake, positioned too far forward or too far back or displaced slightly in the lateral direction; and therefore, the absorption capacity and receiving surface of the entire sanitary towel may not be optimally utilized.

Conventional sanitary towels are generally retained in the briefs of the wearer by means of pressure-sensitive adhesive or friction coatings. The sanitary towel is fitted by the towel being put in place in the briefs, after which the latter are pulled up into position. When fitting the article inside the briefs, however, it is difficult to achieve a positioning which is optimum in relation to the body of the wearer. Use is usually made of the crotch portion of the briefs in order to determine where the sanitary towel should be positioned. As sanitary towels are manufactured in a great many sizes and models, the position and design of the crotch portion provide a particularly uncertain indication of where in the briefs a sanitary towel is to be positioned, and the functioning of the sanitary towel during use is consequently not always as desired.

Another cause of leakage occurring past sanitary towels attached inside the briefs of the wearer is that the sanitary towel moves together with the briefs instead of following the body movements of the wearer. This means that even a sanitary towel which was from the outset positioned correctly in the briefs in relation to the body can be pulled out of this position by the briefs.

In order to attempt to reduce leakage arising as a result of the sanitary towel being pressed together between the legs of the wearer, it has become usual to provide the sanitary towels with special attachment flaps. It is known from, for example, SE 455 668, U.S. Pat. No. 4,285,343, EP 0 130 848, EP 0 134 086 and U.S. Pat. No. 4,608,047 to provide sanitary towels with flexible side flaps or wings projecting from the longitudinal side edges. These are intended to be folded around the edge portions of the briefs of the wearer when the sanitary towel is put on, and to be attached to the outside of the briefs. The side flaps themselves constitute protection against side edge leakage and soiling of the briefs. Moreover, deformation of the absorption body of the sanitary towel is counteracted by virtue of the fact that the sanitary towel is anchored at the leg edges of the briefs and is held extended between these during use.

However, a considerable disadvantage of providing absorbent articles with such attachment flaps is that many wearers find it embarrassing that the attachment flaps are visible on the outside of the briefs. This also means that absorbent articles with such attachment flaps cannot be used when, for example, the wearer is wearing a swimsuit.

Another disadvantage of the attachment flaps is that they are relatively difficult to handle and require many manual operations in order to be fitted correctly around the leg edges of the briefs. Furthermore, especially in the case of attachment flaps which extend quite a long way along the side edges of a sanitary towel, it can be virtually impossible to fold the attachment flaps around the curved leg edges of the briefs without chafing and unattractive creases in the attachment flaps occurring.

A further problem of sanitary towels with attachment flaps is that the functioning of the attachment flaps or wings depends on the design of the briefs. It goes without saying that a sanitary towel with attachment flaps interacts differently with briefs with a wide crotch compared with briefs with a very narrow crotch.

Attachment flaps or wings on sanitary towels protect the leg edges of the briefs from soiling but, for at least the reasons discussed above, are far from being an entirely satisfactory solution.

In order to improve leakproofness, EP 0 067 465 has proposed manufacturing a two-part sanitary towel in which the two parts are interconnected only at their end portions. The lower part is fastened in the briefs of the wearer, and the upper part makes contact with the body of the wearer. The idea is that the parts will be able to move slightly in relation to one another during use. The mobility between the parts is, however, very limited, and the known sanitary towel is still dependent on the movements of the briefs. Furthermore, there is no guarantee that the upper part will be held in contact with the body of the wearer during use.

PCT/SE96/01061, which has now published as WO 9709014, describes another two-part absorbent article in which the two parts are movable in relation to one another.

This known article also has limited mobility between the parts and is to a certain extent dependent on the movements of the briefs.

One way of attempting to reduce the risk of edge leakage caused by deformation of the sanitary towel during use is to provide the sanitary towel with a preshaped raised portion, what is known as a hump, which is intended to make contact with the genitals of the wearer during use of the sanitary towel. Discharged bodily fluid can in this way be caught as soon as it leaves the body of the wearer and be absorbed immediately into the article instead of running out over the surface of the latter. A raised portion also makes it easier for the wearer to position the article correctly in relation to the body. French patent publication FR-A-2 653 328 describes a sanitary towel with a hump in the form of a central, longitudinal, cylindrical raised portion.

A common way of creating a raised portion has been quite simply to build it up by arranging a greater quantity of absorption material within the area of the raised portion. As the absorption material used is in most cases what is known as cellulose fluff pulp, however, such a raised portion collapses and loses its shape when it is wetted. In order to produce a raised portion which is sufficiently large in the wet state as well, a raised portion consisting of cellulose fluff pulp must comprise so much absorption material that it is altogether too high, hard and uncomfortable to wear in the dry state.

It is also known to produce an article with a raised portion facing the wearer by positioning a shaping element on top of the absorbent core. The disadvantage is that this interferes with the liquid transport down to the absorbent, liquid-retaining absorption core and that leakage can occur because the shaping element does not have sufficient admission capacity or temporary retention capacity. The use of, for example, a foamed material in the raised portion has been proposed. However, it has proved difficult to produce a foamed structure with sufficiently open pores for good liquid admission into the latter at the same time as the material is to have such great retention capacity that liquid is not pressed out in the event of loading originating from the wearer, for example when the wearer sits down.

Another example of a raised portion is described in Swedish Patent No. 507 798. Such a raised portion has a predictable shape, both before and during use, and also keeps its shape irrespective of the movements of the wearer and of the wetting to which it is subjected. The raised portion is anatomically designed, which means that it is relatively narrow in order to project in slightly between the labia of the wearer during use without causing discomfort for the wearer.

Although such a raised portion functions well for its purpose, it has been found that when the raised portion is exposed to large quantities of bodily fluid over a relatively short period of time, there is a risk that some of the liquid will run on the outside of the raised portion and flow out past the side edges of the absorbent article. Such leakage can occur, for example, when the wearer of a sanitary towel has been sitting or lying down for a relatively long period of time and then suddenly rises. This is because, when the wearer is sitting or lying down, a relatively large quantity of menstrual fluid accumulates in the vagina of the wearer. In the event of a sudden change in body position, the entire quantity of accumulated liquid may be discharged at once. A narrow raised portion of the type described in SE 507 798 does not then have a sufficiently large surface to be capable of receiving and absorbing the entire quantity of liquid at one time, for which reason such sudden liquid flows often result in leakage.

EP 0 335 252 and EP 0 335 253 have proposed providing an absorbent article with a deformation element. The deformation element is acted on by the transverse compressive forces between the thighs of a wearer. The purpose of the deformation element is to cause a portion of the article to bulge in the direction of the body of the wearer during use. It is impossible, however, to control or predict entirely the shape the article will adopt for each individual wearer. Moreover, it is not possible to ensure contact between the body of the wearer and the surface of the article, because the degree of bulging is determined entirely by how much the article is compressed in the transverse direction.

U.S. Pat. No. 4,804,380 describes an absorbent article which has a permanent three-dimensional shape. The article has one end portion of flat or concave shape and one end portion provided with a raised portion. The flat or concave end portion is intended to be positioned in front of the mons Veneris of the wearer, and the end portion comprising the raised portion is intended to fit in against the buttocks of the wearer. The three-dimensional design of the article is brought about by folding a fairly stiff absorption body. In order to make the raised portion permanent, the rear side of the article is provided with a glued surface in the end portion which is to have the raised portion. When the raised portion has been formed, it is maintained by means of the glue.

There are absorbent articles on the market which have a permanent, three-dimensional, boat-like shape and in which the outer shell consists of a moulded polymer foam.

A considerable disadvantage of permanent three-dimensional products is that it is difficult to pack a stiff three-dimensional product. Such products require a great deal of space for transport and sale, and it can be embarrassing for a wearer to carry around a sanitary towel or an incontinence pad when it is impossible to fold and therefore cannot be concealed in the hand or in the worst case will not even fit in a handbag.

EP 155 515 describes how an absorbent article, such as a sanitary towel, is provided with a bowl-shaped appearance by virtue of elastic being applied in a pretensioned state at the longitudinal side edges of the article. The use of elastic complicates manufacture, and there is a risk of the intended elastic effect being lost in connection with packing of the article or when the latter is stored in a folded packing state.

It is previously known to design plane absorbent articles which adopt a three-dimensional, essentially bowl-like shape when applied. An example of this is described in U.S. Pat. No. 4,655,759, which discloses an elongate sanitary towel consisting of a layer of absorbent material, a flexible liquid-tight outer layer and a liquid-permeable inner layer. The sanitary towel is provided with a pair of channels formed by stamping, the channels being located on both sides of a longitudinal centre axis and extending along a curved path over the absorption material layer. The two paths together form an hourglass-like shape positioned centrally over the towel. Before use, the sanitary towels are essentially plane but, when they are applied to the wearer, they are folded into a bowl-like shape, that is to say with liquid-stopping upright borders outside the channels. One disadvantage of this bowl-like construction is that the borders hold the central portion of the sanitary towel at a distance from the genitals of the wearer, and liquid discharged from the wearer does not flow directly into the absorbent article but can run on the surface, the risk then being obvious that liquid may find an undesirable transport path in the form of a small crease or the like and run straight out of the product in the lateral or longitudinal direction. Stamped channels in an absorption body also have the disadvantage that the liquid spread in the absorption layer is disrupted and that absorption material outside the channels is not utilized, which increases the risk of local oversaturation and attendant leakage from those parts of the absorption layer which are used.

Previously known sanitary towels and the various problems associated with them have in the main been discussed above. However, what has been said above also applies to incontinence pads. Nappies for children and adults also belong to the same problem area as far as fit in the crotch and take-up of liquid in an absorption body are concerned.

As emerged above, great efforts have been made over many years in order to attempt to solve all the problems associated with absorbent articles, such as sanitary towels. Although great improvements have been made, all the previously known solutions are associated with some disadvantages.

SUMMARY OF THE INVENTION

By means of the present invention, an improved absorbent article of the type mentioned in the introduction has been produced. The article according to the invention is characterized mainly in that a stiffening element is in a plane state before use of the article, in that the stiffening element extends in the longitudinal direction of the article over at least part of the rear portion of the article from the crotch portion, in that the stiffening element has in the rear portion at least one elongate second through-hole which extends in the longitudinal direction of the article and along the centre line of the article, as a result of which the article is during use provided, by virtue of lateral forces arising in the rear portion of the article, with a fold along the longitudinal direction of the article along said second hole, which fold extends into the cleft between the buttocks of the wearer during use of the article and in this way stabilizes the article in position on the wearer.

An absorbent article according to the invention has a number of advantages. It is generally planar before use, and there are therefore no problems associated with packing, storing and transporting said article. One advantage of said design is that the article ends up in the correct place on the wearer when it is put on. The fold formed directly in front of and along the second hole holds the article in place in the longitudinal direction in the crotch of the wearer at the same time as the fold formed holds the article in place in the lateral direction by virtue of penetrating the cleft between the buttocks of the wearer.

According to an embodiment, the invention is characterized in that the second hole is pointed at its end next to the crotch portion, and in that the width of the second hole increases continuously from said end in the backward direction, as a result of which the height of the fold increases continuously in the same direction during use of the article.

According to an embodiment, the invention is characterized in that said second hole is located symmetrically and preferably forms an angle of between 10 and 120°, most preferably between 15 and 40°, at said pointed end.

According to a suitable embodiment, the invention is characterized in that the stiffening element also extends over the crotch portion and at least part of the way in over the front portion, in that the stiffening element has a width at the transition between the crotch portion and the front portion which is adapted to the distance between the muscle tendons of the wearer on both sides of the crotch of the wearer in the groin of the latter and which is preferably on the order of 15–45 mm, in that, in the front portion of the article, the side edges of the stiffening element diverge in the direction from the crotch portion at least part of the way in over the front portion, and in that the side edges of the stiffening element form, in the direction from the crotch area, an acute angle with a line in the longitudinal direction of the article.

An absorbent article according to the latter embodiment automatically adopts a three-dimensional bowl-like shape in an area in the front portion next to the crotch portion when the article is, at its transition between the front portion and the crotch portion, fixed in between said muscle tendons. It is known that the distance between said muscle tendons is relatively similar for all people. Fatness of course has an effect on the width between the thighs, but the width between the muscle groups is the same, and it is these which may cause an article to feel as if it chafes. The fat tissue lies on the outside of the muscles but does not contribute to any sensation of discomfort. The distance between said muscle tendons is relatively the same irrespective of whether the wearer is slim, of normal weight or overweight. It has been found that what determines whether a wearer experiences discomfort in the form of pressure or chafing against the insides of the thighs is whether the absorbent article has a width during use which in this subject area considerably exceeds the distance between the muscle tendons in the groin portion. This distance between the muscle tendons has been found to be roughly 25–45 mm. It has been found that an article with a width which exceeds about 40 mm in this subject area during use feels uncomfortable to wear to the majority of wearers. On the other hand, it is rarely experienced as being unpleasant if an absorbent article pushes down or aside fat tissue which may be present in the crotch area of the wearer.

Surprisingly, it has been found that this distance between said muscle tendons does not change throughout the lifetime of a person. Small infants therefore have a corresponding subject distance, which, according to the present invention, can be utilized for producing nappies for infants with an improved fit. The same of course applies for nappies for adults. It should be pointed out that said subject distance between the muscle tendons applies for men also, who have the same distance between said muscle tendons.

An article designed according to the latter embodiment of the invention is particularly well adapted to the anatomy of the wearer. The special geometry around the transition between the crotch portion and the front portion results in an article being anchored firmly in the groins of the wearer during use, and in this way the article is prevented from moving backwards between the legs of the wearer. This is otherwise a common problem in conventional articles because the leg movements of the wearer often shift the article backwards. This, in combination with the fold formed along the second hole, which fold, as mentioned above, holds the article in place on the wearer in both the lateral direction and the longitudinal direction, results in an article according to this embodiment staying in place well on the wearer simply by virtue of its geometry.

According to a preferred embodiment, the invention is characterized in that the stiffening element is absorbent and at the same time constitutes the absorbent element, and in that it swells during absorption while retaining its geometry in the transverse direction of the article.

It is of course possible to have a separate stiffening element behind the absorption element, seen from the side facing the wearer. A completely separate stiffening element, which has only a stiffening function, can consist of an element, made of paper or plastic for example, which is stiff in relation to the rest of the article and can be constructed from one or more material layers made of the same material or different materials. Alternatively, the stiffening area can be brought about by virtue of the article having been stiffened in this area by extra bonding agent between individual material plies. Alternatively, the article can consist of material which is permanently compressible at least in the area which is to be stiffened, suitable compression, if appropriate with heat and/or moisture being supplied, taking place during manufacture of the article to bring about the desired stiffness in the area concerned.

Depending on the selection of absorption material, it may be suitable from the point of view of function to separate the absorption element from the stiffening element. For example, a soft wadding with an open structure for rapid liquid admission and with superabsorbent material mixed in can constitute an effective absorbent material, and such a design likely requires a separate stiffening element. Another example in which a separate stiffening element is preferably used is when use is made of an absorption element in the form of a foam with open pores and superabsorbent material mixed in.

However, in terms of production, it is simpler if a separate stiffening element can be eliminated.

The width of the stiffening element at the transition between the crotch portion and the front portion is preferably on the order of 20–35 mm. It has been found that a width of 30–32 mm at said transition fits well for about 80% of all wearers. According to a further embodiment, the invention is characterized in that said width of the stiffening element at the transition between the front portion and the crotch portion is preferably on the order of 25–30 mm.

The stiffening element suitably has a stiffness on the order of 1–15 N measured according to ASTM D 4032-82. This "Circular Bend Procedure" is described in detail in EP 336 578.

According to a preferred embodiment, the invention is characterized in that the stiffening element consists of a dry-formed fibre mat with a preferred density between 0.15 and 0.75 g/cm$^3$ and a weight per unit area on the order of 100–400 g/m$^2$.

A dry-formed fibre mat of this kind is described in U.S. Pat. No. 5,730,737. The fibre mat produced is very stiff after forming and compression. The fibre mat can be used as it is or be mechanically softened to the desired stiffness.

A way of very accurately forming fibrous webs for use as absorption elements in absorbent articles is described in Swedish patent application 0101393-7. The fibrous webs are formed by air-laying fibres, separate air flows containing fibres being fed to a number "n" of different mat-forming wheels, where "n" is a whole number which is at least 2. Separate web layers are formed on the individual web-forming wheels. The fibrous web is formed by said web layers being combined to form a common fibrous web downstream of the mat-forming wheels, which web has very great manufacturing accuracy by virtue of the manufacturing method. The manufacturing speed and thus the web speed can be very high, and the desired manufacturing accuracy at the web speed concerned is achieved by selecting a sufficiently high number "n" of mat-forming wheels. By virtue of this manufacturing method, very thin fibrous webs can be manufactured with very great accuracy.

According to a suitable embodiment, the article according to the invention is characterized in that the side edges of the stiffening element, which diverge at least part of the way from the crotch portion in over the front portion of the article, are arranged so as to form an angle between a line in the longitudinal direction of the article and each of said side edges on the order of about 35–55°, preferably on the order of about 45°. With this geometry in and around the transition between the crotch portion and the front portion, effective anchoring is obtained without the wearer experiencing any discomfort in the form of chafing or the like.

According to an embodiment, the article according to the invention is characterized in that the crotch portion has a length on the order of 70–120 mm, and in that the side edges of the stiffening element diverge in the direction from the crotch portion at least part of the way from the latter in over the rear portion of the article.

Said length of the crotch portion of the article corresponds to the length of a plane portion in the crotch portion of a woman. The stiffening element according to the last embodiment is therefore anchored both at the front and at the rear at the transition between the crotch portion and the front portion and, respectively, at the transition between the crotch portion and the rear portion, as a result of which an article which is very stable, well fixed and at the same time comfortable during use is obtained.

According to an embodiment, the invention is characterized in that the article is arranged so as, by virtue of the stiffness selected for the stiffening element and by virtue of said geometry around the transition between the crotch portion and the front portion, when the article is positioned in connection with it being put on with the transition between the front portion and the crotch portion between said muscle tendons, to be fixed in between these and in this way be transformed from plane form to three-dimensional form with the front portion curved upwards in relation to the crotch portion and forming a bowl-like shape at least in an area next to the crotch portion.

Further advantageous embodiments of the article according to the invention emerge from the subsequent patent claims.

BRIEF DESCRIPTION OF THE FIGURES

The invention will be described in greater detail below with reference to illustrative embodiments shown in the accompanying drawings, in which.

DETAILED DESCRIPTION OF THE INVENTION

Figure 1:
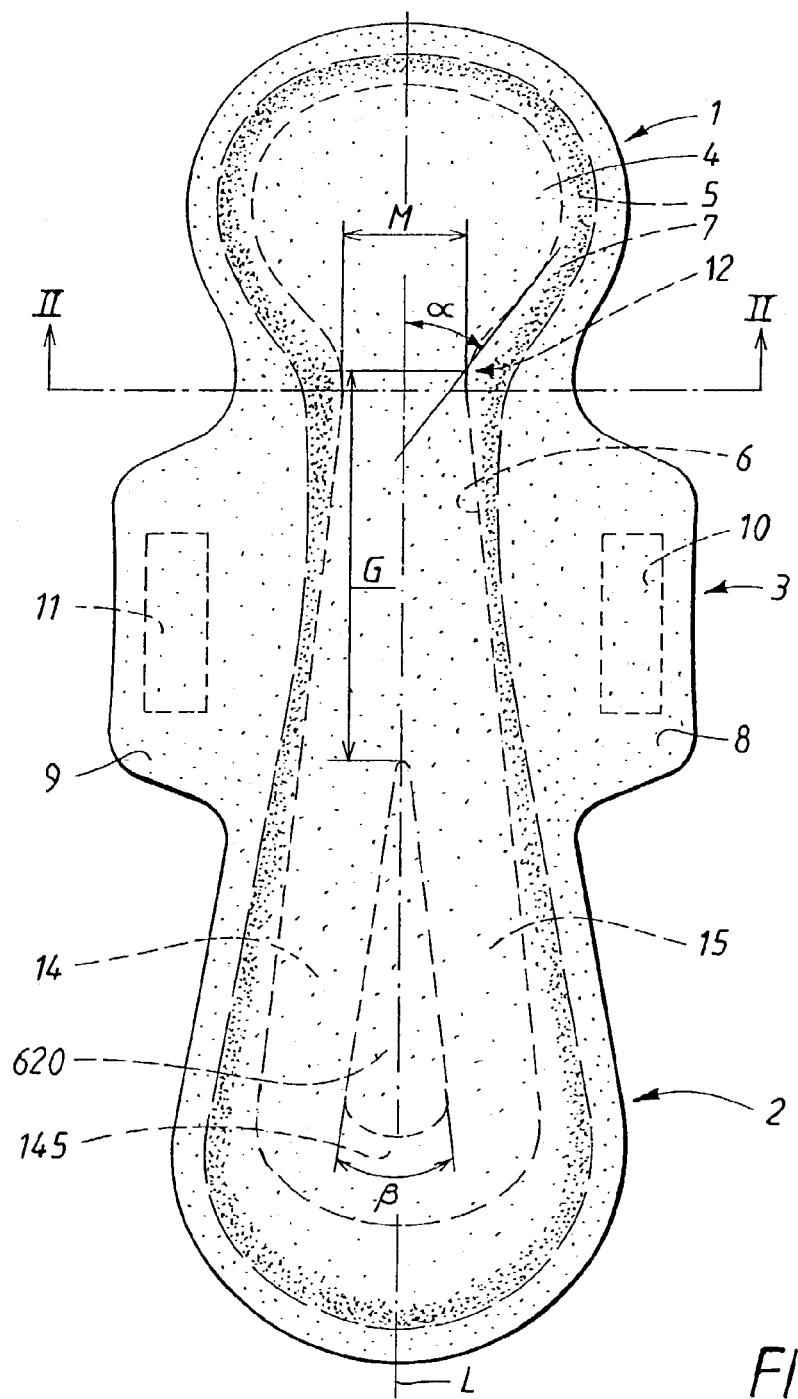
FIG. 1 shows a plan view of an absorbent article according to a first embodiment.
Figure 2:
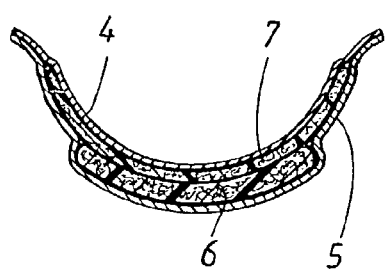
FIG. 2 shows a section along the line II—II in FIG. 1 but in a curved utilization state.

FIGS. 1 and 2 show an article according to the invention in the form of a sanitary towel or incontinence pad. The article is elongate with a longitudinal direction and a transverse direction. The article has a front portion 1, a rear portion 2 and a crotch portion 3 located between said portions. The article shown in FIGS. 1 and 2 comprises an inner layer 4, preferably liquid permeable, which is intended to face the wearer during use of the article. The inner layer, which makes contact directly with the skin of the wearer, is suitably made from a soft, textile-like material. Examples of suitable liquid-permeable materials are various types of what are known as non-woven fabrics. Other examples of suitable materials are perforated plastic films. Net and knitted or woven textiles as well as combinations and laminates of said materials can also be used as the inner layer. Examples of inner layers for sanitary towels are laminates of various non-wovens and laminates of non-wovens and perforated plastic films. The liquid-permeable layer can also be integrated with underlying drainage or absorption layers; for example a foam plastic with open pores and with a density gradient in the depth direction can serve as a surface layer and as a drainage layer and/or absorption layer.

The absorbent article also has a liquid-tight outer layer 5. This usually includes a thin plastic layer, made of polyethylene for example. It is also possible to use a liquid-permeable material which has been treated with a hydrophobing agent in order to make it liquid-tight. In particular if the absorbent article is relatively large, it may be suitable for the outer layer to be breathable and also, if appropriate, vapour-permeable in addition to being liquid-tight. Such layers can consist of hydrophobed non-woven fabric or of porous plastic films.

The embodiment of the absorbent article shown in FIGS. 1 and 2 includes an absorbent element 6 of keyhole-like shape, and a liquid-permeable insulating layer 7 which likewise has a keyhole-like shape but with a greater extent in both the longitudinal direction and the transverse direction than the absorbent element 6. The outer layer 5 and the inner layer 4 extend with edge portions outside the insulating layer around the latter and are interconnected along these edge portions to form a cover around the absorbent element 6 and the insulating layer 7. In the region of the crotch portion 3, the cover formed by the inner and outer layers extends outwards in the lateral direction to form flexible side flaps 8, 9, what are known as wings, which are intended to be arranged around the crotch portion on the briefs of the wearer in order to protect the edge portions of the briefs from soiling. The wings 8, 9 are suitably provided with adhesive coating, which has been indicated in FIG. 1 by reference numbers 10, 11, on the outer layer 5, by means of which the wings can be attached around the legs of the briefs. As can be seen from FIG. 2, the insulating layer 7 is located directly inside the inner layer 4 and is principally intended for rapidly admitting discharged bodily fluid into the underlying absorbent element 6 and forming a liquid-insulating layer so as to reduce what is known as rewet from the absorbent element 6 to the inner layer 4 making contact directly with the wearer.

The insulating layer can be made of, for example, an airlaid fibrous material of low density bonded together with bonding agent or thermofibre, which is marketed under the designation LDA (low density airlaid). The absorbent element 6 is, seen from the liquid-permeable inner layer 4, arranged under the insulating layer 7. In the illustrative embodiment shown here of the article according to the invention, this element is designed to take up and retain essentially all the bodily fluid discharged. The absorbent element 6 can be made from a material which has smaller capillaries than the insulating layer 7 located above and therefore draws liquid from the insulating layer and prevents rewetting by liquid from the absorbent element to the insulating element and to the inner layer 4 which remains essentially dry during use of the article. Only when the absorbent element is saturated with liquid can transport take place from the absorbent element to the insulating layer.

The liquid-insulating layer 7 and the absorbent element 6 can of course be made from materials other than those indicated above. The important aspect is that the absorbent element 6 has greater liquid-affinity than the liquid-insulating layer 7 so that liquid is transported from the insulating layer to the absorbent element but not vice versa.

The liquid-insulating layer can be made of, for example, what is known as a multibond non-woven, that is to say a non-woven fabric in which fibres are bonded by both bonding agent and melt bonds. This can also contain fibres or particles made of a slow-acting superabsorbent material and/or an odour-inhibiting superabsorbent material.

In the illustrative embodiment shown, the absorbent element 6 is also intended to serve as a stiffening element and is to this end designed so as to be stiff in order as far as possible to avoid the absorbent article being compressed in an uncontrolled manner when squeezing forces in the lateral direction occur, generated by the thighs of the wearer in the crotch area. The absorbent stiffening element has a size, shape and stiffness which result in the article, throughout its time of use, retaining a predetermined shape and moreover being retained in the intended position on the wearer.

The expression stiffening area means that an area has been reinforced in some way in order that this area is stiffer than the rest of the article. This reinforcement can include a separate reinforcing element as referred to above which, as in the embodiment according to FIGS. 1 and 2, also serves as an absorbent element, or a completely separate stiffening element which has only a stiffening function and can include an element, made of paper or plastic for example, which is stiff in relation to the rest of the article and can be constructed from one or more material layers made of the same material or different materials. Alternatively, the stiffening area can be brought about by virtue of the article having been stiffened in this area by extra bonding agent between individual material plies. Alternatively, the article can be made of material which is permanently compressible at least in the area which is to be stiffened, suitable compression taking place during manufacture of the article to bring about the desired stiffness in the area concerned. The latter illustrative embodiment is described in greater detail below.

In the description below, the expressions stiffening area and stiffening element will be used interchangeably, the most suitable expression being selected in order to clarify what is meant at the point concerned in the text.

As can be seen from FIG. 1, the absorbent stiffening element 6 extends over the front portion, the entire crotch portion 3 and a considerable part of the rear portion 2.

At the transition 12 between the crotch portion 3 and the front portion 1, the stiffening element 6 has, in the illustrative embodiment shown here, a width M which is adapted to the distance between two particular muscle tendons on both sides of the crotch of the wearer directly in front of the groins. These muscle tendons form part of the muscle group which originates on the inside of the pelvic diaphragm and has its attachment along the thigh. This muscle group includes the adductor brevis, adductor longus, gracilis and adductor magnus muscles. As mentioned above, it is known that the distance between said muscle tendons is relatively similar for all people. This dimension is on the order of 25–45 mm. Research has shown that 80% of all women have a dimension of roughly 30–32 mm between said muscle tendons. When said width M essentially corresponds to the distance between said muscle tendons on the wearer, the article will be anchored firmly during use with the transition portion between the muscle tendons and be retained in this position. The two side edges of the front portion diverge in the forward direction on the article from said transition area 12. In this way, the article is prevented from moving backwards between the legs of the wearer. This is a common problem in conventional sanitary towels because the leg movements of the wearer often shift the sanitary towel backwards.

In FIG. 1, an angle between a line in the longitudinal direction of the article and each of said side edges has been designated by $\alpha$. In the case of a large angle $\alpha$, for example close to 90°, the edges of the front portion may chafe against the groins and legs of the wearer and in this way cause discomfort for the wearer. The smaller the angle $\alpha$, the greater the risk that the article will slide backwards in between the legs of the wearer. In the case of an angle of less than 30°, this risk is generally unacceptably high. An angle of preferably about 35–45° provides the best balance between secure positioning and comfort. An angle of roughly 45° has been found to be especially favourable.

An absorbent article, such as a sanitary towel, according to the invention is designed with a crotch length adapted to the anatomy of the wearer. In a sanitary towel according to the invention, use has been made of the fact that the great majority of women have a crotch length on the order of 80–100 mm. The stiffening element 6 has therefore been designed with a corresponding preferred crotch length G on the order of 70–120 mm, that is to say the distance from the transition area 12 to the start of the rear portion.

Along the crotch, where the body shape of the wearer is essentially plane, the sanitary towel according to the invention is designed so as in the dry state to be relatively stiff in the lateral direction, that is to say it is sufficiently stiff not to be deformed in an uncontrolled manner in the lateral direction and form creases. As the stiffening element 6 in the embodiment described here also constitutes the major part of the absorption capacity of the sanitary towel, it is particularly desirable for it to be possible to utilize available space between the legs of the wearer in the crotch. The width of the sanitary towel in the crotch area is, with regard to the stiffening element, limited at the front by said distance between said muscle tendons directly in front of the groins of the wearer. In the backward direction from said transition area to the end of the crotch portion, the width of the stiffening element 6 and thus the absorbent element can increase continuously on the order of 1.5 times the width in the transition area 12 between the crotch portion and the front portion without any risk of the stiffening element chafing the wearer in the crotch.

The above-mentioned geometrical design of the area in and around the transition area 12, that is to say the size of the angle $\alpha$ and the width M, and also the selected crotch length G on the stiffening element for the article according to the invention, affords a very good anatomical adaptation of the stiffening element, which gives the article a good fit and stability in the fitted position on the wearer. This is of particularly great importance for the functioning of the article, not least because the wetting point can, on account of the body position of the genitals of the wearer in the longitudinal direction of the crotch area, vary for different wearers. As the available space around the wetting point is very limited in width and length, optimum positioning and anchoring in this position of the stiffening absorbent element is necessary. This is achieved by means of said distances M and G selected and said angle $\alpha$ selected.

The anchoring effect is achieved at said muscle tendons even when the width M on the article is slightly less than the distance between said muscle tendons directly in front of the groins. The two edge portions of the front portion diverge in the forward direction, and the article can slide backwards slightly until the edge portions are anchored firmly between said muscle tendons. The distance M on the article is suitably on the order of 15–35 mm and preferably about 25–30 mm. The latter distance fits most wearers. If the distance exceeds roughly 35 mm, articles may therefore feel uncomfortable to some wearers. A distance in excess of 45 mm is generally unsuitable because such articles cause discomfort in the form of chafing for most wearers.

The stiffening element 6 and therefore the absorption element also extend part of the way in over the rear portion 2 of the article. In the rear portion, the stiffening element has an elongate second through-hole 620, as a result of which a weakening is formed so that, during use, the article can fold along a longitudinal line L in the hole 620 and as a result of which the stiffening element forms legs 14 and 15 which are located on both sides of the hole 620 and are more flexible than the wider crotch portion. The legs 14 and 15 can be made slightly vertically movable in relation to one another by virtue of the width selected for the hole. The hole 620 is thus very useful for obtaining the desired adaptation and flexibility of the article in relation to the body. The fold formed along the hole during use of the article can penetrate the cleft between the buttocks of the wearer and in this way provides very good protection against leakage via the cleft between the buttocks, which type of leakage usually occurs during the use of conventional products when the wearer is lying on her back. The fold formed, which projects into the cleft between the buttocks of the wearer, also results in the article being stabilized in position on the wearer and remaining in the intended position during body movements, for example when the wearer is walking. The article is held in place on the wearer in both the longitudinal direction and the transverse direction by the fold formed at the hole 610. The two legs 14 and 15 are interconnected at the bottom at 145. This connection gives the stiffening element 6 very good stability in the rear portion and provides the article with the necessary firmness in this area.

In the illustrative embodiment shown in FIG. 1, the hole 620 is wedge-shaped and located symmetrically in relation to the longitudinal symmetry line L of the article and also forms an angle $\beta$ preferably on the order of 20°. This angle can vary within wide limits but of course depends on the design of the rear portion 2. The angle $\beta$ can vary between the order of 15° and 40°.

The hole 620 is pointed at its end next to the crotch portion 3, and, in the illustrative embodiment shown, the width of the hole increases continuously from said end in the backward direction. As a result of this, the height of the fold formed will increase continuously in the same direction during use of the article, and this increasing height of the fold prevents the article being displaced forwards.

In the illustrative embodiment shown, the stiffening element 6 also serves as the main absorption element of the article and has a liquid-spreading capacity for rapid spreading of bodily fluid received from the wearer in the narrow crotch area directly in front of the genitals of the wearer over the absorbent portions of the whole article, that is to say over the entire stiffened and also liquid-absorbing element 6. This stiffened absorbent element is designed so as to swell in the depth direction during absorption and on the whole retain its geometry in the transverse direction of the article, which results in the stiffening element retaining its fit and secure positioning in relation to the body of the wearer throughout use of the article. The absorbent stiffening element 6 has great swelling capacity in the depth direction and attendant great absorption capacity.

According to a suitable embodiment, the stiffening absorbent element 6 is made of a dry-formed fibre mat with a preferred density between 0.15 and 0.75 g/cm$^3$ and a weight per unit area on the order of 100–400 g/m$^2$. A dry-formed fibrous mass in the form of a fibre mat is described in U.S. Pat. No. 5,730,737. The fibre mat produced is very stiff after forming and compression. The fibre mat can be used as it is or be mechanically softened to the desired stiffness.

A way of very accurately forming fibrous webs for use as absorption elements in absorbent articles is described in Swedish patent application 0101393-7. The fibrous webs are formed by air-laying fibres, separate air flows containing fibres being fed to a number "n" of different mat-forming wheels, where "n" is a whole number which is at least 2. Separate web layers are formed on the individual web-forming wheels. The fibrous web is formed by said web layers being combined to form a common fibrous web downstream of the mat-forming wheels, which web has very great manufacturing accuracy by virtue of the manufacturing method.

The manufacturing speed and thus the web speed can be very high, and the desired manufacturing accuracy at the web speed concerned is achieved by selecting a sufficiently high number "n" of mat-forming wheels. By virtue of this manufacturing method, very thin fibrous webs can be manufactured with very great accuracy.

The fibre mat for forming the stiffening absorbent element can be made of a mixture of cellulose fibres and viscose fibres, the presence of the latter giving the fibre mat a greater wet strength than a fibre mat made of only cellulose fibres. The fibre mat for forming the stiffening absorbent element can also contain synthetic melt fibres, by means of which the strength of the fibre mat can be increased by heat treatment to melt said synthetic melt fibres.

The absorbent stiffening elements can also be formed from foamed material.

A further example of stiffening absorbent material is a laminate in the form of one or more plies of tissue and superabsorbent material (SAPs). The material or combination of different materials serving as an absorbent element and also, if appropriate, as a stiffening element can contain SAPs in the form of fibres, particles or foam.

The selection of compression pattern also makes it possible to vary the extensibility of the fibre mat. The dry-formed fibre mat can be provided with the desired reduced stiffness and the desired extensibility by virtue of the degree of compression selected and the compression pattern selected.

Furthermore, it is possible to pattern-compress only specific zones for the purpose of providing only these zones with an extensibility and stiffness which are different from the rest of the stiffening absorption element. In the same way, the stiffening absorption element can be compressed over its entire extent but with different patterns in different zones. By virtue of the presence of a stiffening absorption element which can in a simple manner, by virtue of the pattern compression selected, be provided with the desired stiffness and the desired extension in different zones, and in which the stiffness and extension properties can be selected essentially freely in these zones, the present invention has brought about a new and previously unknown way of controlling and guiding the shaping of an absorbent article intended for taking up bodily fluids.

As mentioned above, the stiffening absorbent element 6 has great swelling capacity in the depth direction, which has been achieved by great compression of the fibre mat in connection with its production. In the dry state, the material formed, such as the fibre mat, is hard-compressed and stiff, which affords the shaped and anatomically adapted absorption element very good stability in the fitted position on the wearer and very great spreading capacity, as a result of which the total absorption capacity of the absorption element can be optimally utilized and leakage caused by local oversaturation can to a great extent be eliminated. During absorption of liquid, the absorption body swells mainly in the depth direction but the absorption element does of course swell slightly in other directions as well. When the anatomically adapted stiffening absorption element swells, further improved anatomical adaptation is in fact achieved, which contributes to the stability and flexibility of the article in relation to the body shape of the wearer when the stiffness of the absorption element decreases during absorption and attendant swelling.

So as to function in the desired manner, the stiffening element has a preferred stiffness in the dry state on the order of 1–15 N measured according to ASTM D 4032-82. This "Circular Bend Procedure" is described in detail in EP 336 578.

The stiffening absorbent element can also be made of a laminate of a number of non-woven fabric layers or tissue layers which are fixed to one another for increased stiffness and which can have highly absorbent particles between individual plies. The individual plies can be fixed to one another by a bonding agent, such as adhesive or melt fibres. The highly absorbent particles can also contribute to bonding. The stiffness is controlled by virtue of the selection of the number of plies and the quantity of bonding agent included and the selection of highly absorbent material and how the adhesive capacity thereof is utilized.

A stiffening absorbent element of this type can also be provided with different stiffness and different extensibility in different zones of the extent of the element. These properties can in this case as well be controlled by means of compression patterns. This compression can be combined with the supply of heat, which supply can vary in different zones. Furthermore, bonding agent can be applied in different patterns to control the shaping of the stiffening absorption element during use. A varying supply of moisture in different areas in connection with compression is another parameter for controlling the shaping of the article during use.

Another example of the construction of a unit serving as both absorption element and stiffening element is a number of layers of LDA, that is to say layers of the same type as in the drainage and insulating layer 7. However, the layers of LDA in the stiffening absorption element are bonded both within and between individual layers. This bonding is brought about by hard-compression of the LDA layers and suitably by using both melt fibres and latex, what is known as the multibond technique. In this design as well, stiffness and extensibility can be controlled by compression pattern selection and also by variation of the heat supply in different zones.

Further material examples are mixtures of LDA and HDA (high density airlaid) if appropriate in combination with other material layers, such as tissue.

Pattern compression can be used in all the material examples described above, and it is then possible to achieve, for example, hinge effects along compression lines or compression zones.

Pattern formation can take place in connection with compression of the stiffening absorption element. Alternatively, pattern compression can take place in a separate step after smooth compression. Use can be made of, for example, a web of material made in one of the ways described above and smooth-compressed as the starting material for the stiffening absorption element, which is pattern-compressed in the desired manner and depending on the type and size of article to be manufactured. After pattern-compression, individual products are cut out. Pattern-compression and cutting-out of separate stiffening absorption elements can take place in a single step in a combined cutting and pattern-compression unit.

As described above, the stiffening element can also constitute the main absorption element of the article. This is suitable from the point of view of production because there are fewer elements to handle than if, for example, the stiffening element and the absorption element constitute separate elements.

The invention also comprises designs in which the stiffening element is separate from the main absorption element of the article. The stiffening element can then be absorbent or non-absorbent. The main purpose in such a design is to constitute a stiffening shaping element.

In addition to the interpretation of the term stiffening element as constituting a completely separate element or constituting both the main absorption element and the stiffening element of the article, the term can also embrace the interpretation that all the material plies, bonding agents etc. included in the article in the area of the desired stiffening together form the desired stiffening element. In such a design, the expression stiffening area can also suitably be used instead of stiffening element. Absorption element and stiffening area can be made of one and the same material, for example a foamed material or a body constructed from fibres, the stiffening area being bonded in compressed form.

For example, a unit serving as a stiffening element and also as an absorption element, with the M and G dimensions indicated above and with the geometry described above but with stiffness which is in itself inadequate, is included in the invention if the necessary stiffness is obtained by being bonded together with other material plies in the area of the stiffening element.

Figure 3:
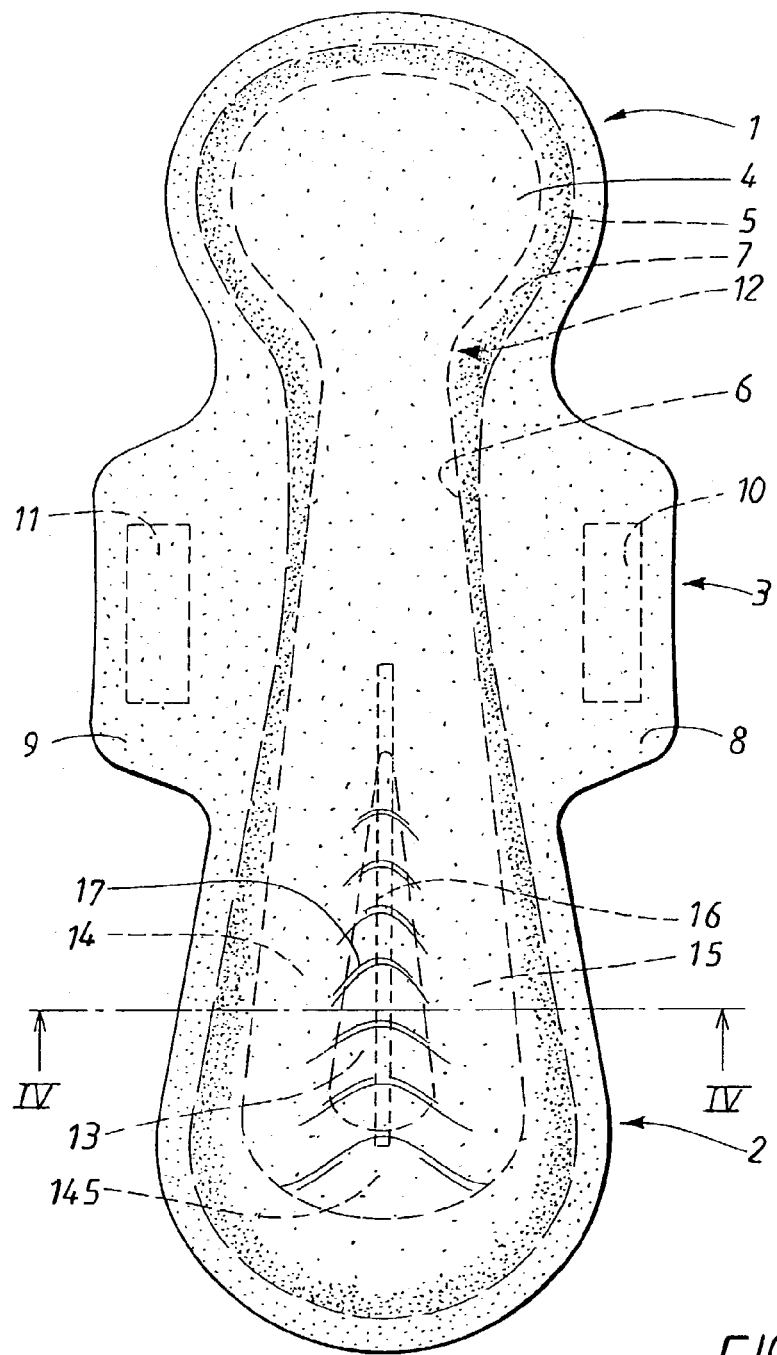
FIG. 3 shows an embodiment, slightly modified in relation to the embodiment according to FIG. 1, of an article according to the invention in a plan view.
Figure 4:
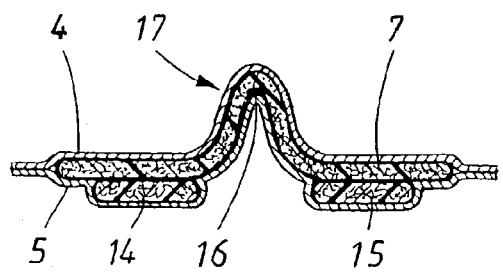
FIG. 4 shows a section along the line IV—IV in FIG. 3.

The embodiment shown in FIGS. 3 and 4 differs from the embodiment shown in FIGS. 1 and 2 only in that an elastic means 16 is arranged in a pretensioned state in the longitudinal direction of the article and centrally along the rear portion 2 of the article. The same reference numbers have been used in FIGS. 3 and 4 as in the embodiment according to FIGS. 1 and 2.

The elastic means 16 is arranged centrally in the hole 620 and extends in the rear portion slightly beyond the ends of the legs 14 and 15, under the portion 145 connecting the legs and, in the other direction, part of the way over the crotch portion. The elastic means is arranged on the inside or on the outside of the liquid-tight outer layer and is connected to the latter and/or other layers forming part of the article. The extent of the elastic means 16 is not critical but can vary somewhat in relation to the illustrative embodiment shown in FIG. 3. One purpose of the elastic means 16 is, during use of the article, to draw adjacent material portions together and contribute to curving the article in the upward direction towards the body of the wearer for better contact with the body. Another purpose is also to initiate and form the fold 17 which, during use of the article, is intended to penetrate part of the way into the cleft between the buttocks of the wearer, stabilize the article in position on the wearer and also prevent leakage of bodily fluid backwards along the cleft between the buttocks, which leakage can otherwise occur when the wearer is lying on her back.

Figure 5:
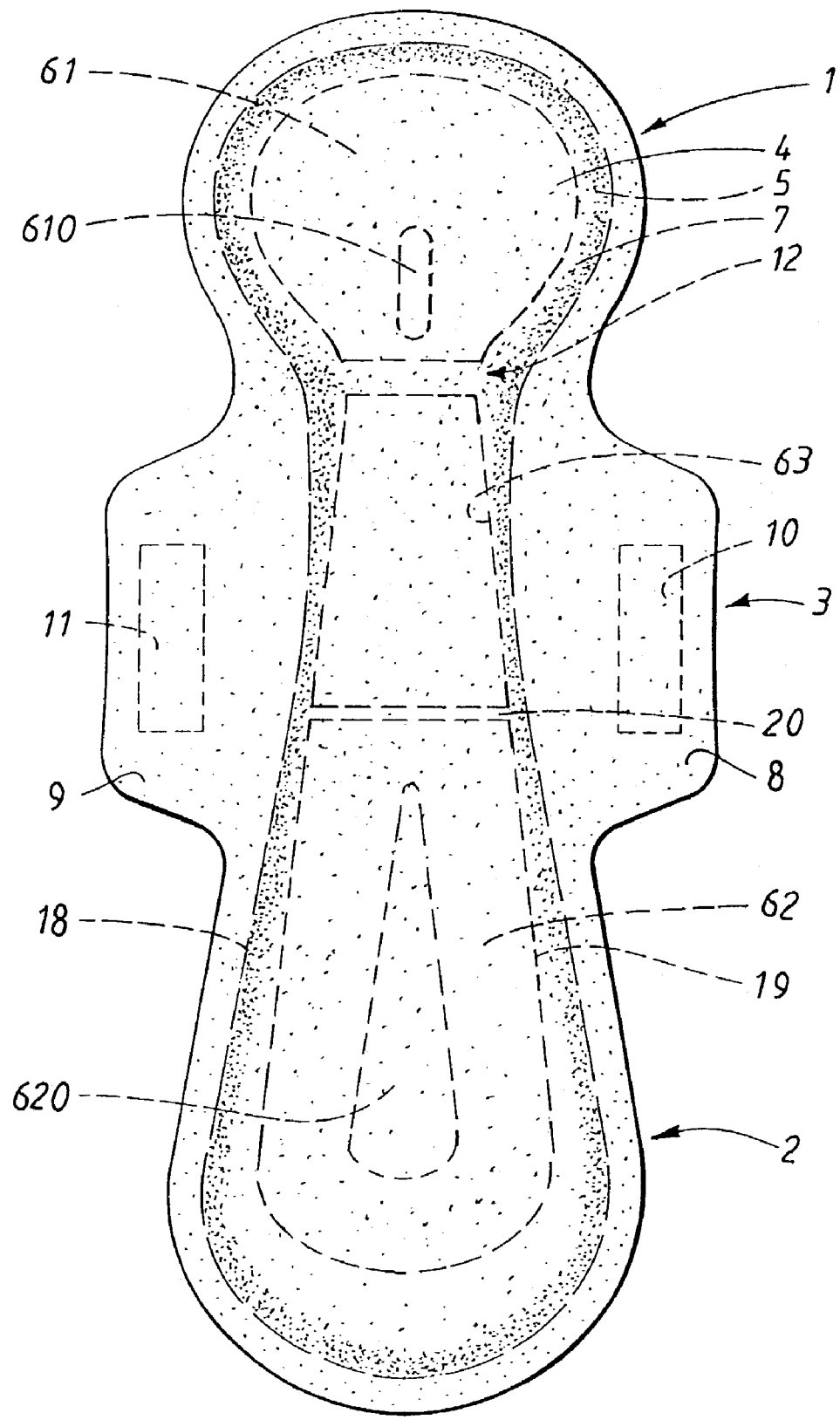
FIG. 5 shows a plan view of a third embodiment of the article according to the invention.

In the embodiment shown in FIG. 5, the components which correspond to similar parts in the embodiments according to FIGS. 1–4 have been provided with the same reference numbers. The embodiment according to FIG. 5 includes a stiffening element which is designated as a whole by reference number 6 and includes a first stiffening part element 61 in the front portion 1 and a second part element 62, separate from the first part element, in the rear portion. Arranged between the two part elements 61, 62 is an absorbent crotch element 63. In the illustrative embodiment shown, the absorbent crotch element 63 is designed to be less stiff than the stiffening part elements 61, 62 in order as far as possible to avoid the absorbent crotch element giving rise to chafing when squeezing forces in the lateral direction occur, generated by the thighs of the wearer in the crotch area. The absorbent crotch element 63 is retained in the intended position by means of the stiffening part elements 61, 62.

At the transition 12 between the crotch portion 3 and the front portion 1, the stiffening part element 61 has a width M which, as in the embodiments described above, is adapted to the distance between said muscle tendons on both sides of the crotch of the wearer directly in front of the groins. The two side edges of the front stiffening part element 61 diverge in the forward direction on the article from said transition area 12. In this way, the article is prevented from moving backwards between the legs of the wearer when the wearer is walking. By virtue of the first stiffening part element 61 being separate from the absorbent crotch element at the transition 12, a certain turning of the first part element 61 in relation to the crotch element 63 and also in relation to the second part element 62 is permitted, which makes increased mobility possible for the wearer without the risk of annoying chafing caused by the stiffening part elements 61, 62.

In the embodiment shown in FIG. 5, the first stiffening part element 61 has been provided with an elongate first through-hole 610, and the second stiffening part element has an elongate second through-hole 620 with the same function as the elongate second hole in the embodiments according to FIGS. 1–4. The stiffening part elements forming part of the embodiment according to FIG. 5 can be made of the same material as described above in connection with the description of the stiffening element 6 in the embodiments according to FIGS. 1–4.

As can be seen from FIG. 5, the first through-hole 610 arranged in the first part element is oblong and extends along the longitudinal direction of the article and along its centre line. The purpose of the first hole 610 is to facilitate curvature of the first part element and to make possible resilient compression thereof in the lateral direction when lateral forces against the side edges of the first part element arise.

The outer side edges 18, 19 of the second part element diverge in the direction from the crotch area. The purpose of the edge sides 18, 19 of the second stiffening part element 62 diverging in the backward direction on the rear portion 2 is that the article, in addition to being anchored firmly at the transition 12 between the front portion and the crotch portion, will also be anchored at the rear in the transition area between the crotch portion 3 and the rear portion 2, as a result of which the article is very stable and well fixed on the wearer during use at the same time as it feels comfortable for the wearer by virtue of its anatomical adaptation in terms of shape, size and geometry. For a good anchoring function, the angle between the longitudinal direction of the article and each outer edge side 18, 19 should preferably not be less than roughly 30°. Furthermore, so as not to feel uncomfortable, the angle should preferably not exceed roughly 60°.

The distance G between the transition area 12 and a transition area 20 between the crotch element and the second stiffening part element 62 is adapted to the crotch length of a wearer and, as mentioned above in connection with the embodiments according to FIGS. 1–4, this distance G is suitably on the order of 70–120 mm. As mentioned above, the essentially plane area of the crotch of women directly in front of the genitals has a length on the order of 80–100 mm, that is to say all women are essentially the same size in this plane area. It has been found that having a crotch dimension G on the article on the order of 70–120 mm functions well for most wearers. The larger the angles between the side edges of the first part element and the longitudinal direction of the article and between the outer edge sides 18, 19 and the longitudinal direction of the article, and the stiffer the stiffening element, the more important it is that the crotch dimension on the article corresponds to the length of the plane crotch portion of the intended wearer directly in front of her genitals if the article is not to feel uncomfortable.

It may therefore be conceivable to have a range of sizes of the article according to the invention depending on the selection of stiffness and said angles, so that different wearers can find a suitable size with regard to dimensions and angles. This of course applies to all the embodiments of the invention described here but is particularly important when the article is intended to be anchored both at the front and at the rear. The requirement for size adaptation also increases for all the embodiments the stiffer the absorbent element is.

The second stiffening part element 62 in the rear portion 2 of the article is provided with an elongate second hole 620. As in the other illustrative embodiments described above, this hole is wedge-shaped and has the same function, that is to say it is to give rise to a fold 17 during use of the article, which fold stabilizes the article in the fitted position on the wearer in both the lateral direction and the longitudinal direction.

As mentioned above in connection with the other illustrative embodiments, the size of the hole 620 also influences the height of the fold 17.

FIGS. 6–9 show a suitable embodiment of an article according to the invention. This embodiment corresponds in many respects to the embodiments according to FIGS. 1–4, and those parts corresponding to the same parts in the embodiments described above have been provided with the same reference numbers in the drawing.

Figure 9:
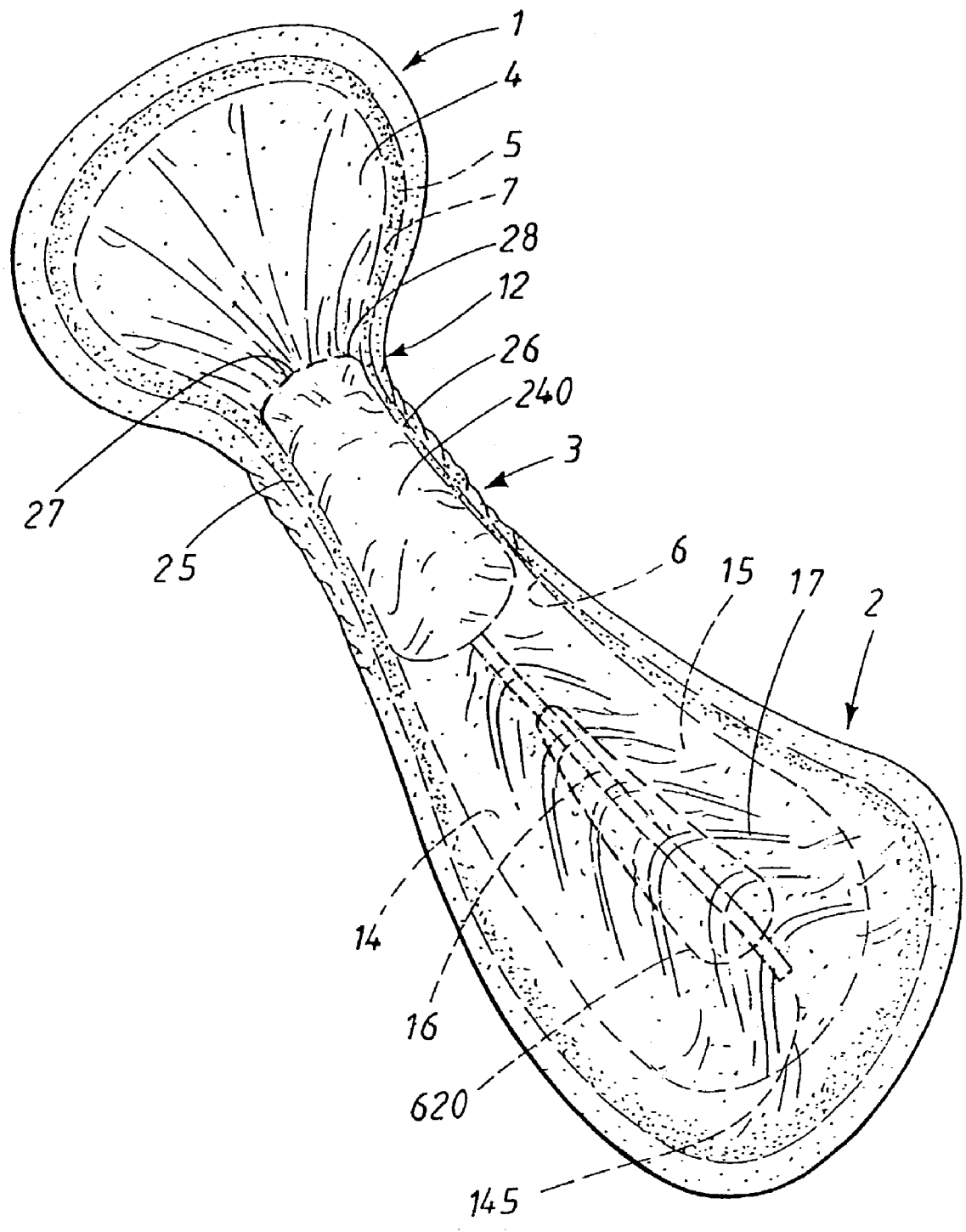
FIG. 9 shows, in perspective and in a utilization state, the article according to the fourth embodiment and also the embodiment shown in FIGS. 6–8.

A way of reducing further the risk of edge leakage caused by the sanitary towel being deformed during use, in addition to the arrangement of the stiffening element 6, is to provide the sanitary towel with a raised portion, what is known as a hump, which raised portion has been designated by reference number 240 (FIG. 9). The raised portion or hump is intended to make contact with the genitals of the wearer during use of the sanitary towel. Discharged bodily fluid can in this way be caught as soon as it leaves the body of the wearer and be absorbed immediately into the article instead of running out over the surface of the latter.

Figure 7:
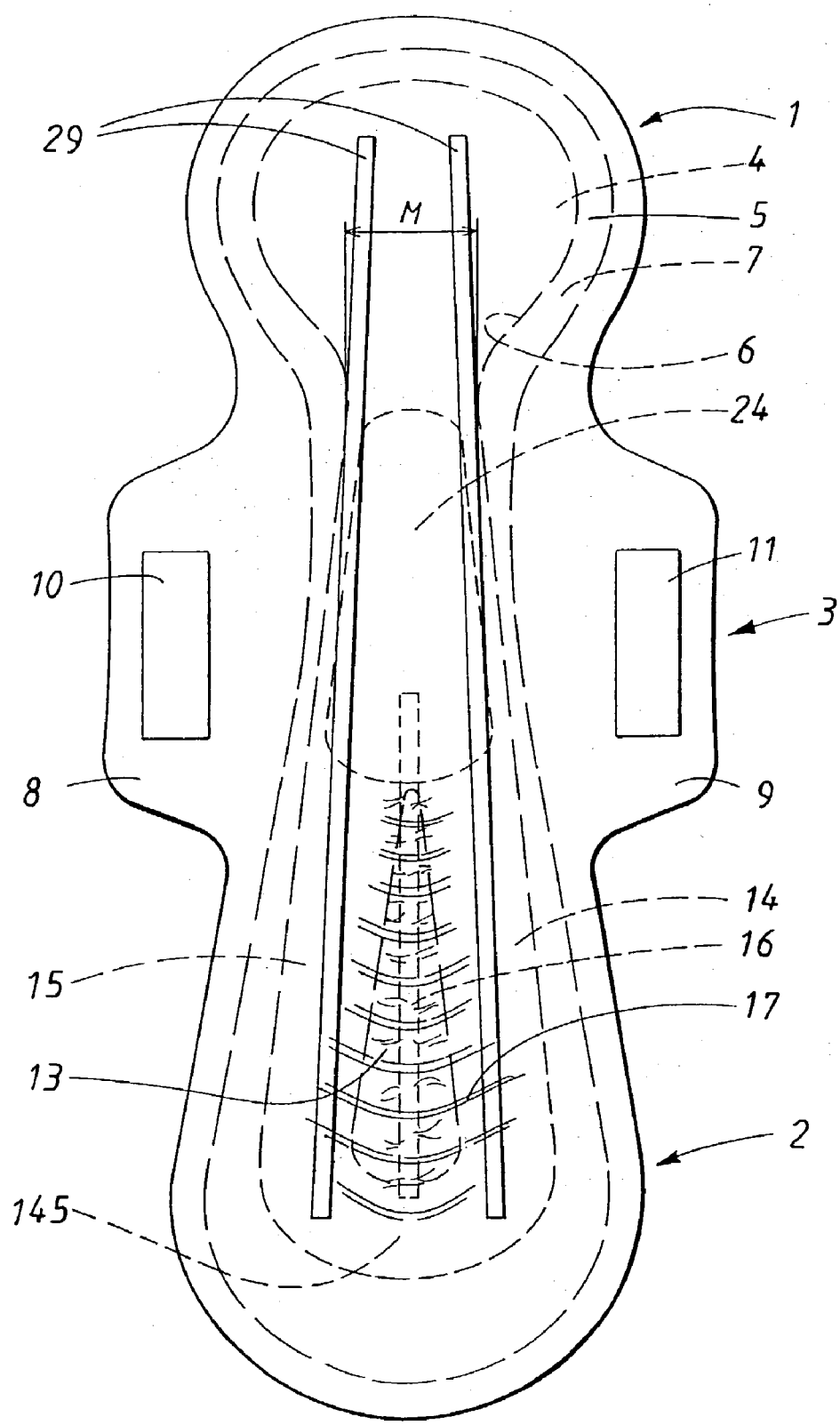
FIG. 7 shows a plan view of the article according to FIG. 6 from the opposite side.
Figure 8:
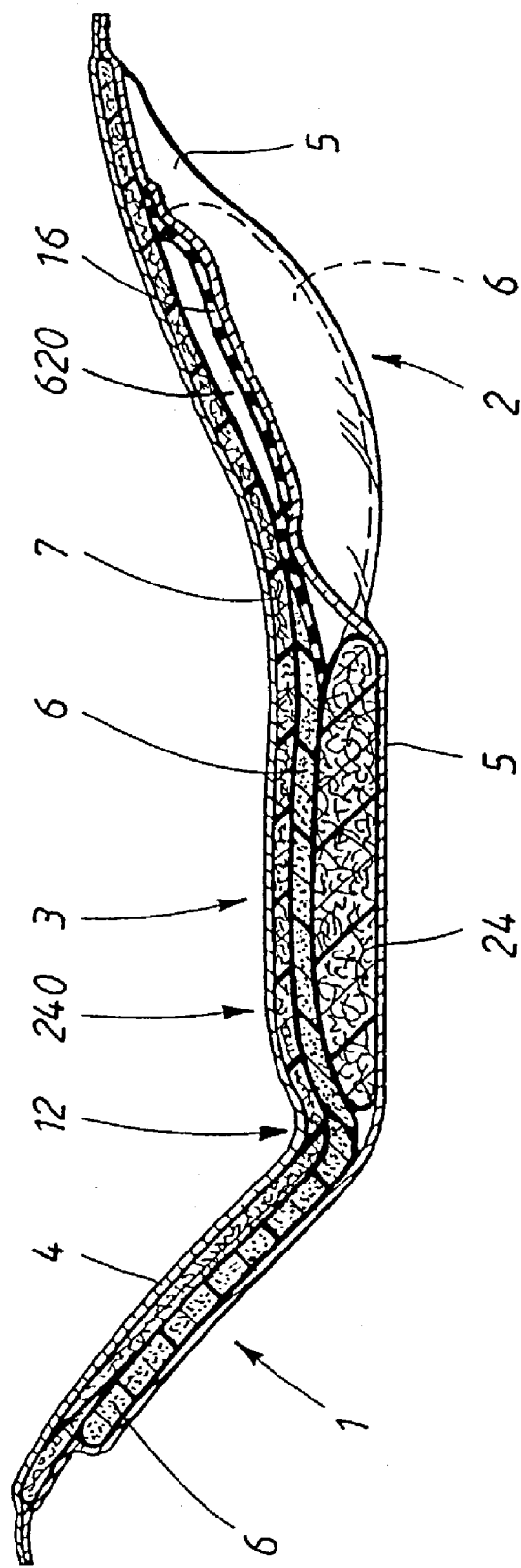
FIG. 8 shows a section along the line VIII—VIII in FIG. 6 but in a curved utilization state.

In the embodiment shown in FIGS. 6–9, the hump is brought about by a hump-forming element 24 which, as can be seen most clearly from FIG. 8, is arranged below the stiffening element 6 inside the liquid-impermeable outer layer 5. The positioning of the hump-forming element results in a number of advantages. Admission of bodily fluid is not interfered with by hump material in direct proximity to the genitals of the wearer, but the parts located closest to the genitals of the wearer can be optimized with regard to admission and absorption capacity. The positioning selected for the hump-forming element below the stiffening element 6 in combination with the positioning along the crotch portion of the article also results in the positive effect that the article curves and shapes itself in the desired manner when fitted on the wearer. At the transition 12 between the crotch portion 3 and the front portion, as can be seen from FIG. 9, a point of inflection 27 is formed, in front of which, that is to say in the front portion of the article, the article is concave at least over a portion next to said transition 12. Behind said point of inflection, that is to say along the crotch portion of the article, the article is, in the area directly in front of the hump-forming element 24, convex, that is to say the stiffening element 6 is curved in this area, upwards in the crotch portion 3, as can be seen most clearly from FIGS. 8 and 9. In addition to bringing about the raised portion 240 on the front side of the article, the hump-forming element makes it possible to guide the stiffening element in the desired direction of curvature at different points of the extent of the stiffening element.

The hump-forming element 24 is made of, for example, a non-absorbent synthetic wadding which has resilient properties. Such a hump-forming element retains its shape and function even when the material is in a wet state.

The hump-forming element can also consist of a foamed material, for example polyurethane foam or the like. If appropriate, the hump-forming element can be provided with superabsorbent material, in the form of particles or fibres, which material expands greatly during liquid absorption and expands the hump formed by the hump-forming element.

As the hump-forming material is, in the embodiment shown, located below the absorbent element 6, which also serves as the stiffening element, the hump-forming material can be liquid-absorbing. In such a design, it is suitable to select a material which has larger capillaries than the absorption element has, so that liquid can be transported to the hump-forming material only when the absorption element is saturated with liquid. A hump-forming absorbent fibrous layer which has resilient properties only in the dry state can therefore also be used in such a construction because the material is essentially dry until the absorption element itself is saturated with liquid. The positioning of the hump-forming element 24 below both the stiffening and the absorbent element therefore affords a number of important advantages.

The element forming the raised portion 240 has an elongate shape and extends over the entire crotch portion in the illustrative embodiment shown. The length of the raised portion can preferably vary between roughly 20 mm and 120 mm.

The element 24 forming the raised portion is narrower than the rest of the article in the crotch area. In this way, it is made possible for laterally surrounding portions 25, 26 of the rest of the article to shape themselves around the element 24 forming the raised portion. The material forming the raised portion is suitably at least twice as thick as the surrounding areas 25, 26.

In FIG. 8, the article has been shown in curved, three-dimensional form for the sake of clarity. An absorbent article of the type described here is of course always three-dimensional in the conventional sense, that is to say it has length, width and thickness.

In this context, however, the term three-dimensional means that the article must be curved in some way to adapt to the body shape of the wearer.

In this context, the term plane state or plane form means that the article is essentially plane or planar. The article shown in FIGS. 6 and 7 is essentially in plane form according to this definition in spite of the fact that the elastic means draws the material layers together in the second hole 620 between the legs 14, 15.

Figure 6:
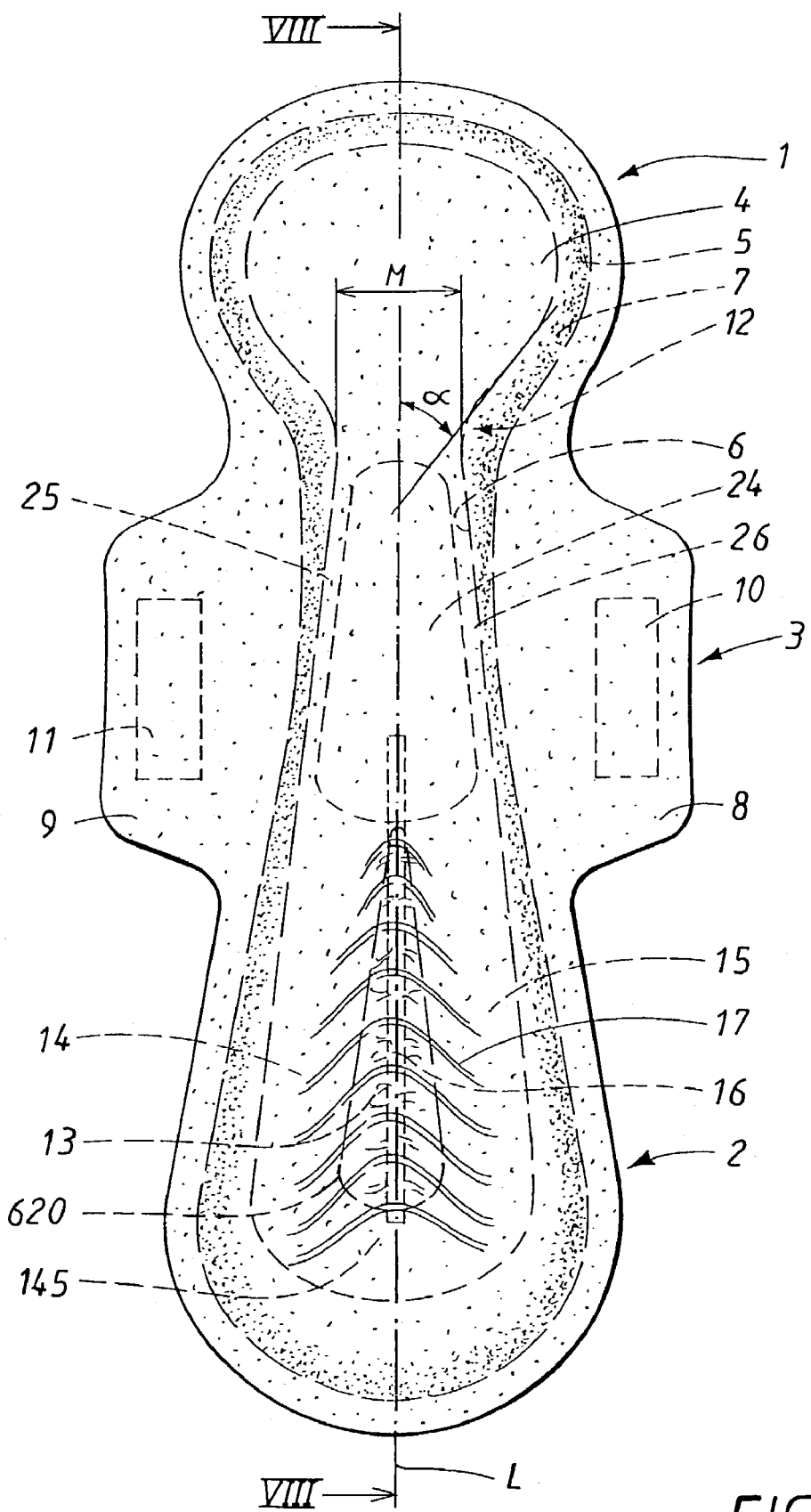
FIG. 6 shows a plan view of a fourth embodiment of the article according to the invention seen from that surface of the article which receives bodily fluids.

Articles in plane form according to FIGS. 6 and 7 can be packed simply, for example in stacks in a box or bag and yet, when put on, be made to adopt an anatomically adapted three-dimensional shape, as shown in FIGS. 8 and 9, without any measures whatsoever.

By virtue of its special design with the dimension of the distance M between said muscle tendons, the hump-shaped element 24, the action of the elastic means 16 and the stiffness and geometric shape of the stiffening element 6, the article is anatomically adapted and predestined to adopt during handling a three-dimensional shape according to FIGS. 8 and 9 adapted to the body shape of the wearer.

In the illustrative embodiment shown, the stiffening and also absorbent element 6 has the same stiffness properties over its entire extent. As a result, uncontrolled creases, which could give rise to uncontrolled and unintentional liquid flow, do not normally arise over the extent of the stiffening element. At the transition 12 between the crotch portion 3 and the front portion 1, curvature is initiated because the article as a whole changes its flexural resistance here, on the one hand on account of the hump-forming element having its end directly in front of this transition and on the other hand because the stiffening element is narrowest here with a dimension M adapted to the distance between said muscle tendons on the wearer. At this transition 12, a point of inflection 27 is formed, in front of which the article is concave and bowl-shaped, whereas it adopts a convex shape behind this point of inflection 27. In the embodiment according to FIG. 9, the hump-forming element is rounded at the front along a line 28. In this way, the stiffening element is caused by this rounded line to adopt an evenly rounded bowl shape in the front portion, as can be seen from FIG. 9.

In the transition area 20 between the crotch portion 3 and the rear portion 2 as well, the hump-forming element 24, which in the embodiment shown extends as far as said transition area 20, is rounded at its rear end. As a result, no undesirable creases arise, but the transition between the convex crotch portion and the two side portions of the rear portion 2 sloping downwards around the fold 17 formed by the elastic means 16 is even and smooth without undesirable creases.

The raised portion 240 formed by the hump-forming element 24 also has the advantage that the fold extending into the cleft between the buttocks of the wearer does not extend in too abruptly or too far and give rise to chafing. In this respect also, the hump provides a soft transition in the transition area between the crotch portion and the rear portion.

In all the embodiments described above, it is suitable for the article to be provided with a pressure-sensitive adhesive on the outside of its liquid-impermeable outer layer 5. This has been indicated in FIG. 7 by adhesive strands 29 which, before use of the article, are covered in a conventional manner by a cover strip 30 treated with release agent. Although the article according to the invention is anatomically adapted, it is suitable, for reliable secure positioning, to have a pressure-sensitive adhesive on the liquid-impermeable outside of the article for interaction with the briefs of the wearer, which contributes to keeping the article in the intended position on the wearer. The selection of suitable attachment, that is to say whether and to what extent pressure-sensitive adhesive for attachment to the briefs of the wearer is to be used, is guided by the selection of the stiffness of the stiffening element included.

According to an embodiment (not shown in the drawing), the article can be attached to or interact with the body of the wearer by means of adhesive or friction coating. The friction means or adhesive can be the only means of attachment, but it can also be used in combination with pressure-sensitive adhesive intended for attachment to the briefs of the wearer.

Figure 10:
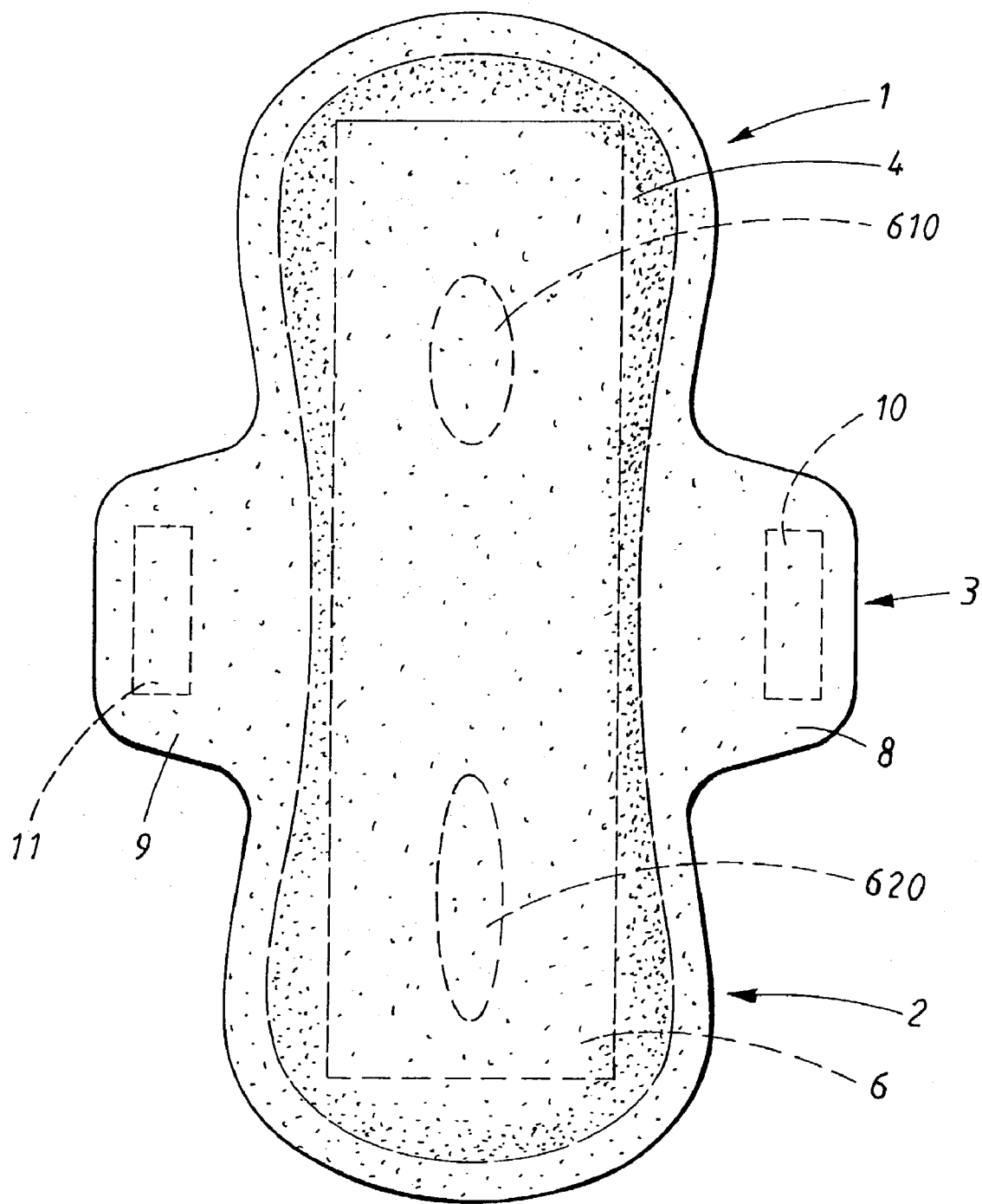
FIGS. 10–12 show plan views of three further embodiments of articles according to the invention.

FIG. 10 shows an embodiment which is modified slightly in relation to the embodiments described above. Those parts in the article according to FIG. 10 corresponding to similar components in the embodiments according to FIGS. 1–9 have been provided with the same reference numbers.

The stiffening element 6 in the embodiment according to FIG. 10 is rectangular and has an elongate through-hole 610 at the transition 12 between the front portion 1 and the crotch portion 3. This hole is intended to make possible pressing-together of the stiffening element 6 in the lateral direction, which pressing-together is at a maximum where the hole is widest when pressing-together takes place. During pressing-together, curvature of the article also takes place, the outer portions of the stiffening element 6 at the front being curved upwards towards the body of the wearer. After pressing-together, the stiffening element 6 has a width M during use which is adapted to the distance between said muscle tendons on both sides of the crotch of the wearer directly in front of the groins. The desired width M is controlled by the stiffness and width of the stiffening element and also by the width of the hole at the point concerned.

As can be seen from the above, it is the first through-hole 610 which makes it possible to press the article together at the transition 12. By virtue of the selection of the stiffness of the stiffening element, the shape and size of the hole and also the material width of the stiffening element in the area directly in front of the hole, the desired resilience can be obtained when the article is pressed together. The result of this is that an article of a certain size can fit wearers with slightly different widths between said muscle tendons, that is to say the hole 610 can be pressed entirely or partly together during use of the article.

After an article according to FIG. 10 has been pressed together during use, the two side edges of the front portion diverge in the forward direction on the article from said transition area 12. In this way, the article is prevented from moving backwards between the legs of the wearer when leg movements take place. In the case of the embodiment according to FIG. 10, essentially the same shape of the front portion of the article and the transition area is therefore obtained during use of the article as in the case of the articles preshaped with anatomically adapted outer contours according to the embodiments described in connection with FIGS. 1–9.

In the rear portion, the stiffening element 6 has an elongate through-hole 620 which extends, backwards in the longitudinal direction of the article and centred along the centre line of the article, from the transition area 20 between the crotch portion 3 and the rear portion. During use, the article is thus, as in embodiments described above, provided with a fold along the longitudinal direction of the article along said second hole 620. During use of the article, this fold extends into the cleft between the buttocks of the wearer and stabilizes the article in position on the wearer.

Figure 12:
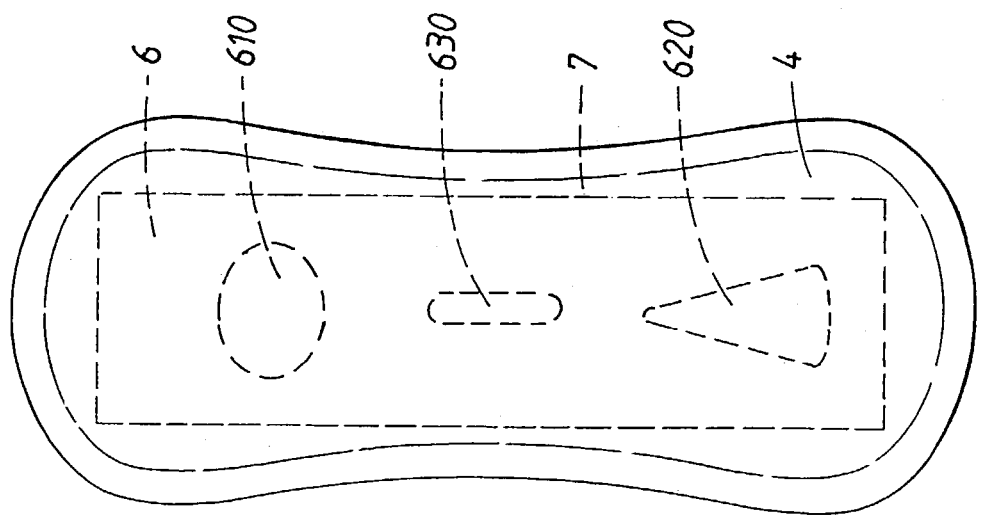
Figure 11:
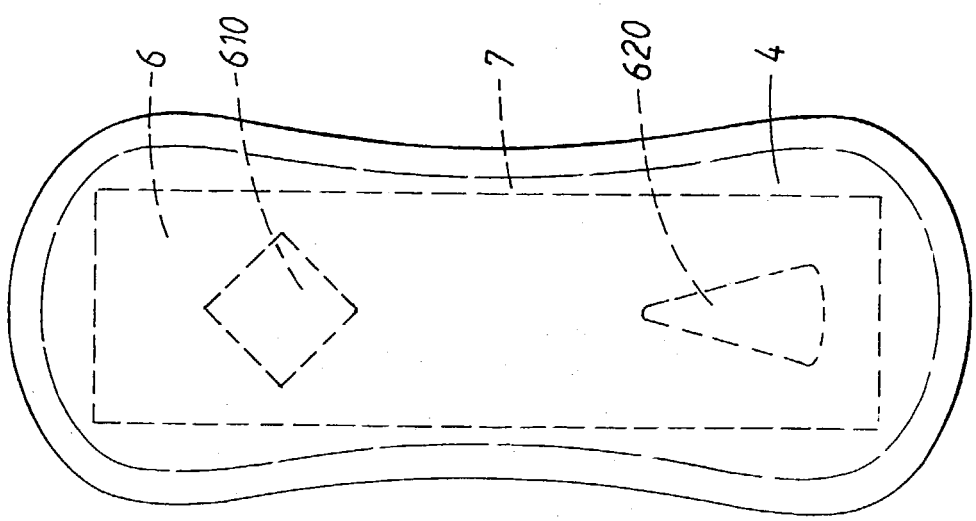

FIGS. 11 and 12 show further examples of the stiffening element for an absorbent article according to the invention. In the embodiments according to FIGS. 11 and 12, those parts corresponding to similar components in illustrative embodiments described above have been provided with the same reference numbers.

In the embodiment according to FIG. 11, the stiffening element 6 extends over the front portion 1, the crotch portion 3 and the rear portion 2 of the article. In the front portion, the stiffening element is provided with a diamond-shaped through-hole 610 which is widest in the transition area 12 where the article is intended to be anchored between said muscle tendons during use of the article. By means of the triangular hole, continuously decreasing curvature of the stiffening element is obtained from said transition 12 in the direction towards the front end of the article.

In the rear portion 2 of the article, as in the embodiments according to FIGS. 1–10, a longitudinal hole 620 is arranged. This has the same function as described in said embodiments and, during use of the article, gives rise to a fold, the height of which increases in the backward direction. During use of the article, the fold stabilizes it in the lateral direction as described above.

FIG. 12 shows an article, the stiffening element 6 of which, as in the embodiment according to FIG. 11, extends over the front portion 1, the crotch portion 2 and the rear portion 3 of the article. In this case, the stiffening element has an elliptical hole 610 directly in front of the transition 12, which hole is intended, during use of the article, to make possible squeezing-together of the stiffening element at the transition 12 to bring about a narrowing in this area to a width M which corresponds to the distance between said muscle tendons on the wearer. A longitudinal hole 630 is arranged in the crotch area of the article. The purpose of the hole 630 is to provide the stiffening element with resilient properties in the crotch area for optimum adaptation of the width of the stiffening element in the crotch area to the body shape of the wearer in this area. The hole 620 has the same function as the corresponding hole in the embodiment according to FIG. 15 and is therefore not described further.

Figure 13:
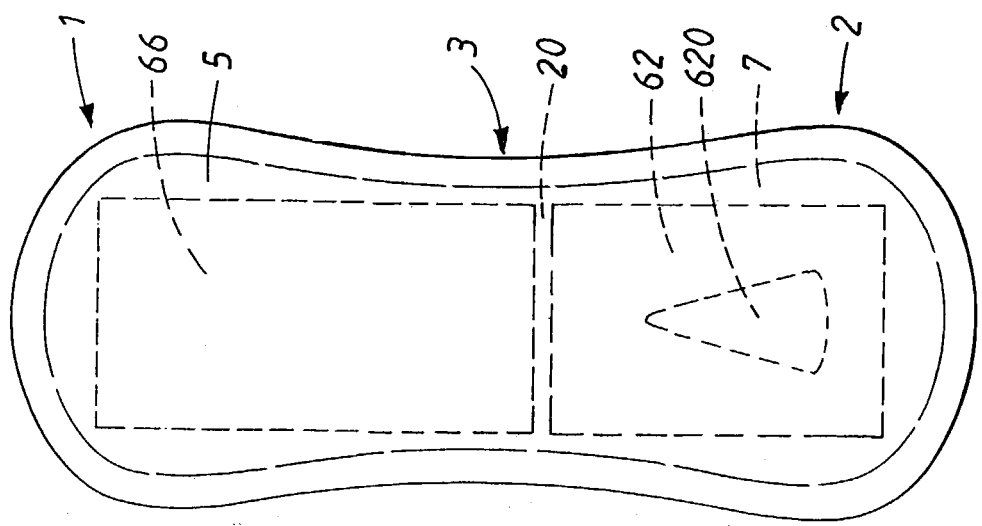
FIG. 13 shows a plan view of an absorbent article according to a further embodiment.

FIG. 13 shows an embodiment which differs from embodiments described above mainly in that the stiffening element consists of only a part element 62 in the rear portion 2 of the article. The part element 62 is rectangular and has an elongate hole 620 of the same kind and with the same function as described in illustrative embodiments described above.

There is no stiffening element in the front portion 1 or in the crotch portion 3. Arranged here instead is an elongate absorption element 66 which is preferably less stiff than the part element 62.

During use of an article according to FIG. 13, the article is held in the intended position on the wearer by means of the stiffening part element, the fold of which formed along the hole 620 stabilizes the article in the lateral direction and in the longitudinal direction on the wearer. The fold projects into the cleft between the buttocks of the wearer and therefore stabilizes the article in the lateral direction. Moreover, the height of the fold increases continuously in the backward direction corresponding to the continuously increasing width of the hole in the same direction, which results in an article fitted on the wearer being stabilized against displacement in the longitudinal direction of the article.

The flexural rigidity of the article increases after it has been fitted on the wearer, which, as mentioned above, is on account of the rear portion of the article being more stable. The fold formed along the hole 620 will, during use of the article, penetrate part of the way into the cleft between the buttocks of the wearer and in this way in addition contribute to the article staying in place in the lateral direction at the same time as catching any bodily fluid which runs in the cleft between the buttocks of the wearer.

As mentioned above, a person has essentially the same dimension M throughout his or her life. Articles according to illustrative embodiments described above therefore function in principle for both children and adults if the article as a whole is adapted in terms of size.

An article according to the invention in the form of a nappy for children or adults has a superior fit compared with conventional nappies. The presence of the stiffening element means that, when the nappy is put on, it is guided into the correct position on the wearer and that it remains in this position during use of the article.

Figure 14:
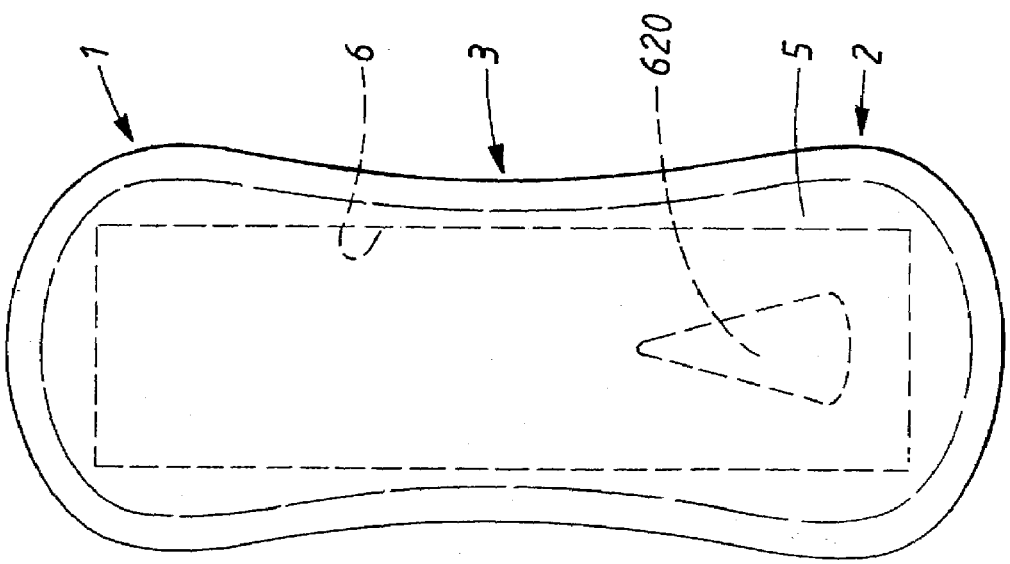
FIG. 14 shows a plan view of an absorbent article according to a further embodiment.

FIG. 14 shows an embodiment in which the stiffening element 6 is rectangular. As in previous illustrative embodiments, a longitudinal hole 620 is arranged in the rear portion of the article. This hole has the same function as described above and, during use of the article, gives rise to a fold, the height of which increases in the backward direction. During use of the article, the fold stabilizes it in the lateral direction, as described above. The same reference numbers have been used in FIG. 14 as in previously described illustrative embodiments.

Figure 15:
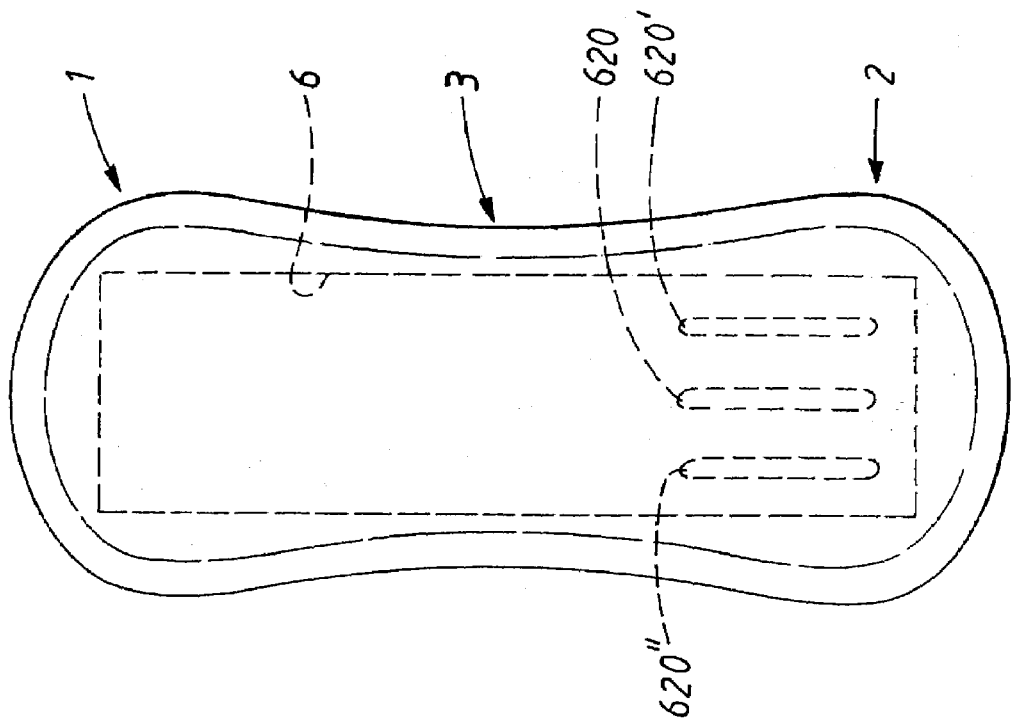
FIG. 15 shows a plan view of an absorbent article according to a further embodiment.

In the embodiment shown in FIG. 15, the article has been provided with three elongate holes 620, 620' and 620" in the rear portion, which holes are positioned symmetrically in relation to the width of the article in the embodiment shown here.

The invention is not limited to the illustrative embodiments described above, but a large number of modifications are possible within the scope of the patent claims below.

For example, anatomically shaped stiffening and absorbent elements of the type described above can be arranged in what are known as pant nappies, that is to say where the nappy is integrated into disposable pants.

It has been stated above that the stiffening absorbent element can be made from different materials and from laminates made of one or more material(s). The stiffening absorbent element can also be made from more than one layer and with the extent of the individual layers being different, in which way it is possible for different areas of the stiffening element to have different stiffness.

As mentioned above, the stiffening element can consist of all the material layers and bonding agents included. Different stiffness in different areas of the stiffening element can therefore also be obtained by varying the degree of connection in different areas, for example different quantities of adhesive in different areas and even the absence of adhesive or other bonding agent in different areas between or in individual layers.

The elastic means 16, which is arranged along the hole 620, has been indicated in the illustrative embodiments described above as having been arranged in a pretensioned state. However, in the manufacture of absorbent articles such as sanitary towels, nappies and the like, it is known to arrange a heat-sensitive elastic means in an untensioned state and to tension the elastic by heat treatment. This suitably takes place when the articles are packed.

In the illustrative embodiments described above relating to articles for arrangement inside the crotch portion of briefs, the article is in the majority of the illustrative embodiments provided with permanently arranged wings for attachment of the article to the briefs with the wings folded around the edge portion of the briefs and attached on the outside of the crotch portion. The wings can consist of separate elements which are attached to the rest of the article in connection with the article being put on. The separate wings can be arranged detachably on the rest of the article during manufacture of the article, as a result of which a wearer who does not want to have wings on the article can remove these in connection with putting the article on.

The illustrative embodiments described above which do not have wings can be provided with separate wings either during manufacture or when the article is put on.

The invention claimed is:

1. An absorbent article having a longitudinal direction and a transverse direction, said absorbent article comprising:
a front portion, a rear portion, and a crotch portion located between the rear portion and the front portion,
an absorbent element and a liquid-tight layer, and
a stiffening element which is intended to contribute to a three-dimensional shape of the article during its use, wherein the stiffening element is in a flat, two-dimensional planar state before use of the article said stiffening element extends in the longitudinal direction of the article over a substantial part of the front, crotch, and rear portions of the article extending rearward from the crotch portion,
wherein the stiffening element is foldable and the stiffening element has at least one elongate through-hole which extends in the longitudinal direction along the centre line over substantially the entire rear portion of the article, as a result of which the article during use is provided, by virtue of lateral forces arising in the rear portion of the article, with a a plurality of stacked curvilinear folds spaced apart from one another by a length and said folds extending in a longitudinal direction from the rear portion to the crotch portion of the article along said through-hole, said folds extend into the cleft between the buttocks of the wearer during use of the article and in this way stabilizes the article in position on the wearer; and wherein the at least one elongate through-hole is pointed at an end next to the crotch portion, and the width of the elongate through-hole is pointed at an end next to the crotch portion, and the width of the elongate through-hole is pointed at an end next to the crotch portion, and the width of the elongate through-hole increases continuously from said end in the backward direction, as a result of which the height of the fold increases continuously in the same direction during use of the article.

2. An article according to claim 1, wherein said at least one elongate through-hole is located symmetrically and forms an angle (β) of between 10 and 120° at said pointed end.

3. An article according to claim 1, wherein the stiffening element also extends over the crotch portion and at least part of the way in over the front portion, the stiffening element has a width (M) at a transition between the crotch portion and the front portion which is adapted to the distance between the muscle tendons of the wearer on both sides of the crotch of the wearer in the groin of the latter and which is on the order of 15–45 mm, such that in the front portion of the article, the side edges of the stiffening element diverge in the direction from the crotch portion at least part of the way in over the front portion, and the side edges of the stiffening element form, in the direction from the crotch area, an acute angle (α) with a line in the longitudinal direction of the article.

4. An article according to claim 3, wherein the stiffening element is absorbent and at the same time constitutes the absorbent element, and it swells during absorption while on the whole retaining its geometry in the transverse direction of the article.

5. An article according to claim 3, wherein said width (M) of the stiffening element at the transition between the crotch portion and the front portion is approximately 20–35 mm.

6. An article according to claim 3, wherein said width (M) of the stiffening element at the transition between the crotch portion and the front portion is approximately 25–30 mm.

7. An article according to claim 3, wherein the stiffening element has a stiffness in the dry state approximately 1–15 N measured according to ASTM D 4032-82.

8. An article according to claim 3, wherein the stiffening element includes a dry-formed fibre mat with a density between 0.15 and 0.75 $g/cm^3$ and a weight per unit area approximately 100–400 $g/m^2$.

9. An article according to claim 8, wherein the dry-formed fibre mat is, after compression, mechanically softened to the desired stiffness.

10. An article according to claim 9, wherein the dry-formed fibre mat is provided with the desired reduced stiffness and the desired extensibility by virtue of the degree of compression selected and the compression pattern selected.

11. An article according to claim 3, wherein the side edges of the stiffening element, which diverge at least part of the way from the crotch portion in over the front portion of the article, are arranged so as to form the angle (α) between a line in the longitudinal direction of the article and each of said side edges which is approximately 35–55°.

12. An article according to claim 3, wherein the crotch portion has a length (G) approximately 70–120 mm, and the side edges of the stiffening element diverge in the direction from the crotch portion at least part of the way from the crotch portion in over the rear portion of the article.

13. An article according to claim 1, wherein the stiffening element also constitutes the absorbent element, it has a stiffness of at least 1.0 N, and it is designed with essentially the same stiffness over the entire extent of the stiffening element.

14. An article according to claim 1, further comprising a hump-forming element made of a resilient material arranged under the absorbent element over at least part of the crotch portion, which hump-forming element is arranged so as to bring about a raised portion on the side which is intended to be fitted against the wearer, the raised portion being arranged so as to come to lie directly in front of the genitals of the wearer after fitting of the article on the wearer.

15. An article according to claim 14, wherein the raised portion is elongate in the longitudinal direction of the article and has a length of between 20 mm and 120 mm.

16. An article according to claim 14, wherein the raised portion is narrower than a remainder of the article in the crotch area, and the raised portion is at least twice as thick as surrounding areas.

17. An article according to claim 1, further comprising an elastic means arranged in the longitudinal direction of the article and centrally along the rear portion of the article and along at least part thereof from the crotch portion, which elastic means is intended, along its length, to draw adjacent material portions together and curve the article upwards for better contact with the body of the wearer.

18. An article according to claim 1, wherein the stiffening element serves as an absorption means and has a liquid-spreading capacity for spreading bodily fluid received in the relatively narrow crotch area bounded by the anatomy of the wearer directly in front of the genitals of the wearer over the absorbent portions of the whole article, and the stiffening element is designed with a swelling capacity in the depth direction and attendant absorption capacity.

19. An article according to claim 18, wherein the stiffening element also serves as an absorption element and is essentially homogeneous over its entire extent with regard to thickness, stiffness, spreading capacity and absorption capacity, as a result of which the stiffening element and thus also the absorption element curve evenly during use without forming local irregularities which may give rise to undesirable spreading of liquid.

20. An article according to claim 3, wherein a length of said transition between the crotch portion and the front portion, at which the width of the stiffening element is adapted to the distance between the muscle tendons of the wearer on both sides of the crotch of the wearer in the groin of the latter, is approximately 5–15 mm.

21. An article according to claim 3, wherein the stiffening element also constitutes the absorbent element, and the width of the stiffening element after said transition increases continuously in the crotch portion in the backward direction towards the rear portion for the purpose of optimally utilizing available width space in this area with regard to maximum absorption.

22. An article according to claim 3, wherein the article is arranged so as, by virtue of the stiffness selected for the stiffening element and by virtue of the selection of said geometry and dimensions in and around the transition between the crotch portion and the front portion, when the article is positioned in connection with it being put on with the transition between the front portion and the crotch portion between said muscle tendons, to be fixed in between these and in this way be transformed from plane form to three-dimensional form with the front portion curved upwards in relation to the crotch portion and forming a bowl-like shape at least in an area next to the crotch portion.

23. An article according to claim 1, wherein said absorbent article is selected from the group consisting of a sanitary towel, a panty liner, an incontinence pad and a nappy.

24. An article according to claim 2, wherein said through-hole forms the angle ($\beta$) of between 15 and 40° at said point.

25. An article according to claim 11, wherein the angle ($\alpha$) formed between the line in the longitudinal direction of the article and each of said edges is approximately 45°.

* * * * *